United States Patent
Galligan et al.

(10) Patent No.: US 9,757,117 B2
(45) Date of Patent: Sep. 12, 2017

(54) METHOD AND APPARATUS FOR FORMING A SUTURE CONNECTOR IN SITU

(71) Applicant: Medtronic Vascular, Inc., Santa Rosa, CA (US)

(72) Inventors: Darren Galligan, San Francisco, CA (US); Jeffery Argentine, Petaluma, CA (US); Benjamin Morris, Jeffersonville, IN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 138 days.

(21) Appl. No.: 14/732,844

(22) Filed: Jun. 8, 2015

(65) Prior Publication Data
US 2015/0265271 A1    Sep. 24, 2015

Related U.S. Application Data

(63) Continuation-in-part of application No. 14/180,016, filed on Feb. 13, 2014, now Pat. No. 9,629,620.

(51) Int. Cl.
*A61B 17/04* (2006.01)
*A61B 17/00* (2006.01)

(52) U.S. Cl.
CPC ...... *A61B 17/0401* (2013.01); *A61B 17/0057* (2013.01); *A61B 17/0467* (2013.01);
(Continued)

(58) Field of Classification Search
CPC ........ A61B 17/0401; A61B 2017/0488; A61B 17/0487; A61B 2017/0409; A61B 17/0485; A61B 17/0467
See application file for complete search history.

(56) References Cited

U.S. PATENT DOCUMENTS

| 3,989,049 A | 11/1976 | Yoon |
| 5,931,844 A | 8/1999 | Thompson et al. |

(Continued)

FOREIGN PATENT DOCUMENTS

| WO | WO0166001 | 9/2001 |
| WO | WO2007001936 | 1/2007 |
| WO | WO2015122987 | 8/2015 |

OTHER PUBLICATIONS

PCT/US2016/036475, International Search Report and The Written Opinion of the International Searching Authority, dated Aug. 30, 2016.

(Continued)

*Primary Examiner* — Thomas McEvoy

(57) ABSTRACT

A system for forming a suture connector in situ includes a suture connector placement device having a handle, an outer shaft, an intermediate shaft, and a push rod, and a suture connector having a sleeve and a plug. The intermediate shaft is slidingly disposed through a lumen of the outer shaft, and the push rod is slidingly disposed through a lumen of the intermediate shaft. When the suture connector is in a loaded configuration within the suture connector placement device, the sleeve is radially disposed over the intermediate shaft and the plug is positioned proximal to the sleeve within the lumen of the intermediate shaft. Distal advancement of the push rod moves the plug into the sleeve and proximal retraction of the intermediate shaft releases the resilient sleeve onto the plug, thereby securing two suture portions between the sleeve and the plug. The system is then utilized to trim the suture portions.

20 Claims, 28 Drawing Sheets

(52) U.S. Cl.
CPC .............. *A61B 17/0487* (2013.01); *A61B 2017/00663* (2013.01); *A61B 2017/0488* (2013.01)

(56) References Cited

U.S. PATENT DOCUMENTS

| | | |
|---|---|---|
| 5,948,001 A | 9/1999 | Larsen |
| 6,117,144 A | 9/2000 | Nobles et al. |
| 6,562,052 B2 | 5/2003 | Nobles et al. |
| 7,803,167 B2 | 9/2010 | Nobles et al. |
| 8,197,497 B2 | 6/2012 | Nobles et al. |
| 8,469,975 B2 | 6/2013 | Nobles et al. |
| 2004/0147941 A1 | 7/2004 | Takemoto et al. |
| 2006/0200199 A1 | 9/2006 | Bonutti |
| 2008/0281356 A1 | 11/2008 | Chau et al. |
| 2010/0121349 A1 | 5/2010 | Meler |
| 2010/0256679 A1 | 10/2010 | Ducharme |
| 2011/0029012 A1 | 2/2011 | Tegels |
| 2013/0158600 A1 | 6/2013 | Conklin et al. |
| 2014/0276975 A1 | 9/2014 | Argentine |
| 2014/0276976 A1 | 9/2014 | Argentine |

OTHER PUBLICATIONS

PCT/US2015/011519 International Search Report and The Written Opinion, dated Apr. 8, 2015.

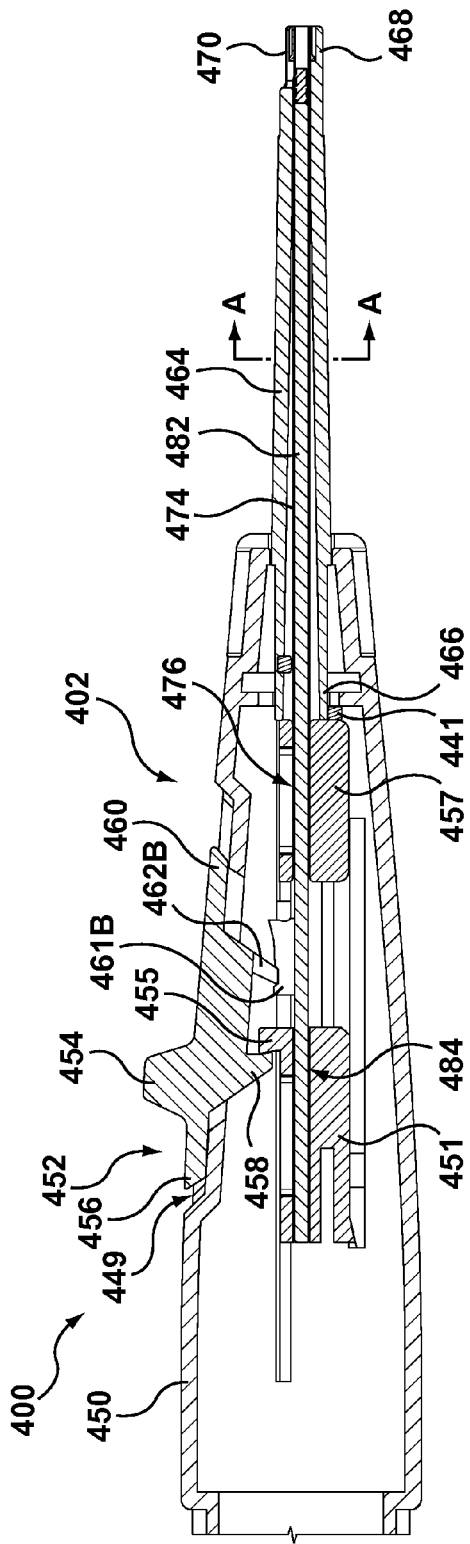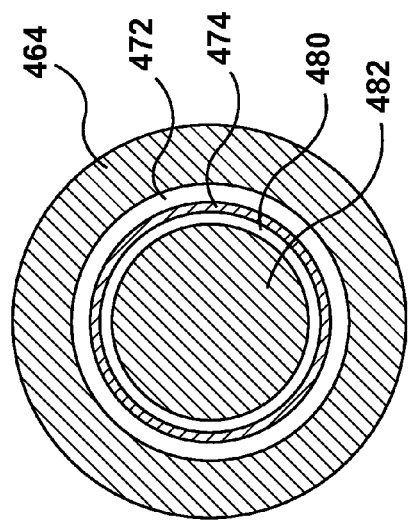
FIG. 6
FIG. 6A

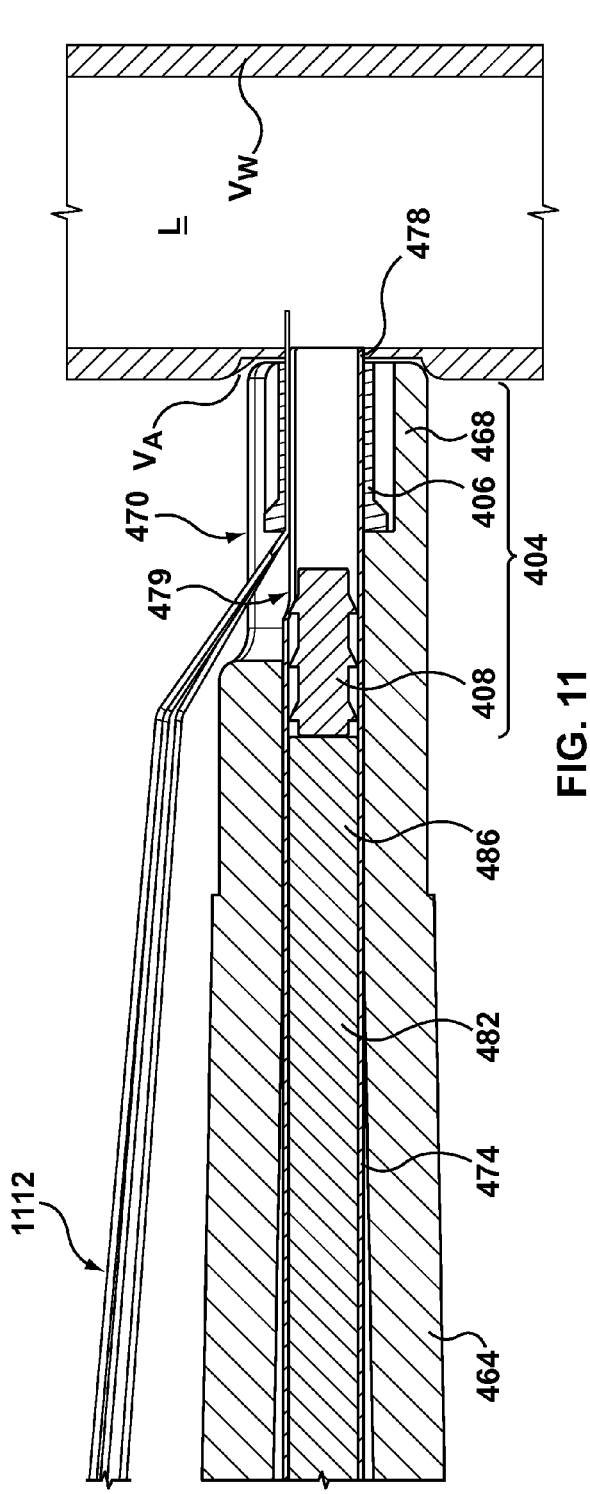
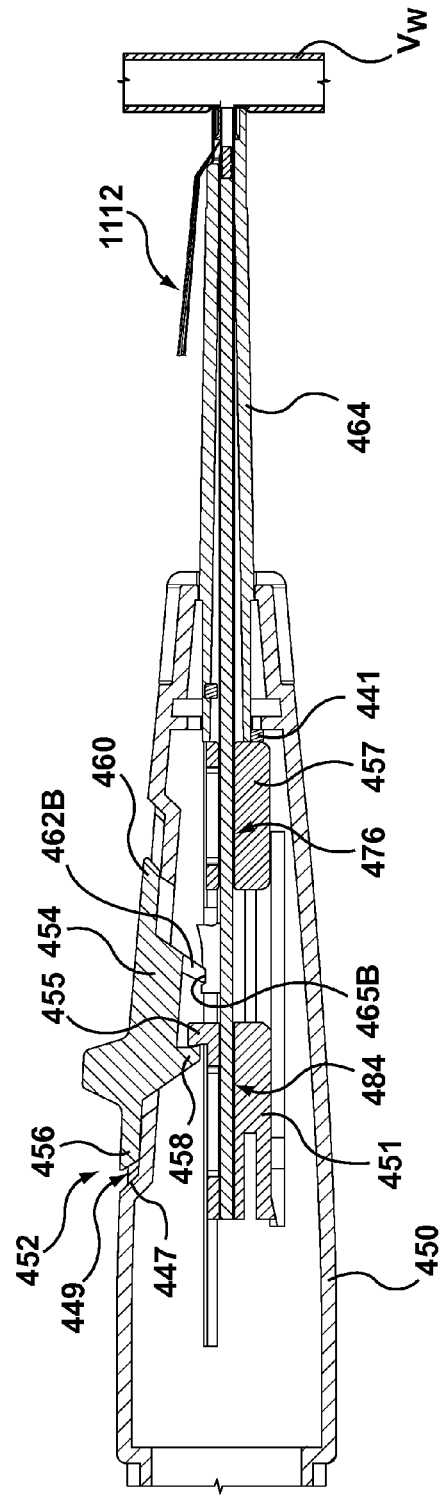

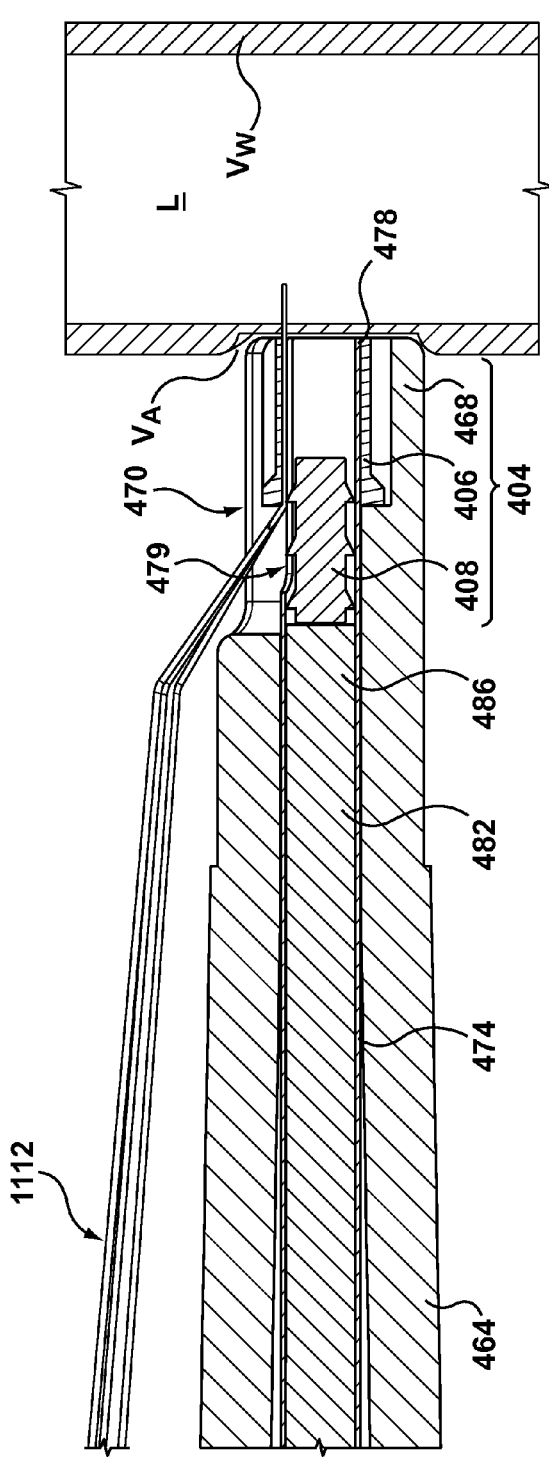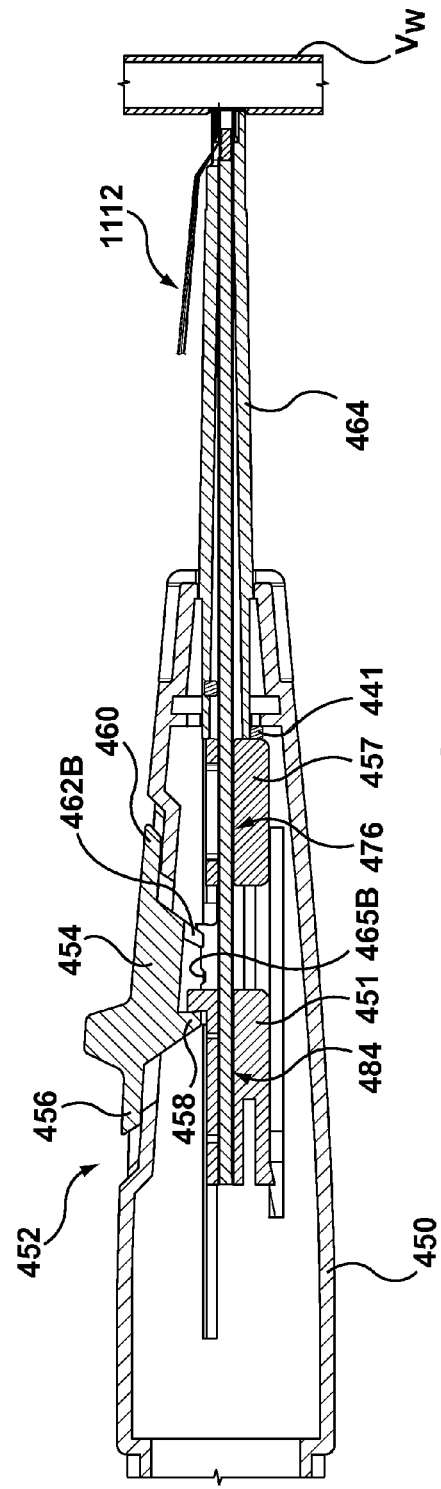

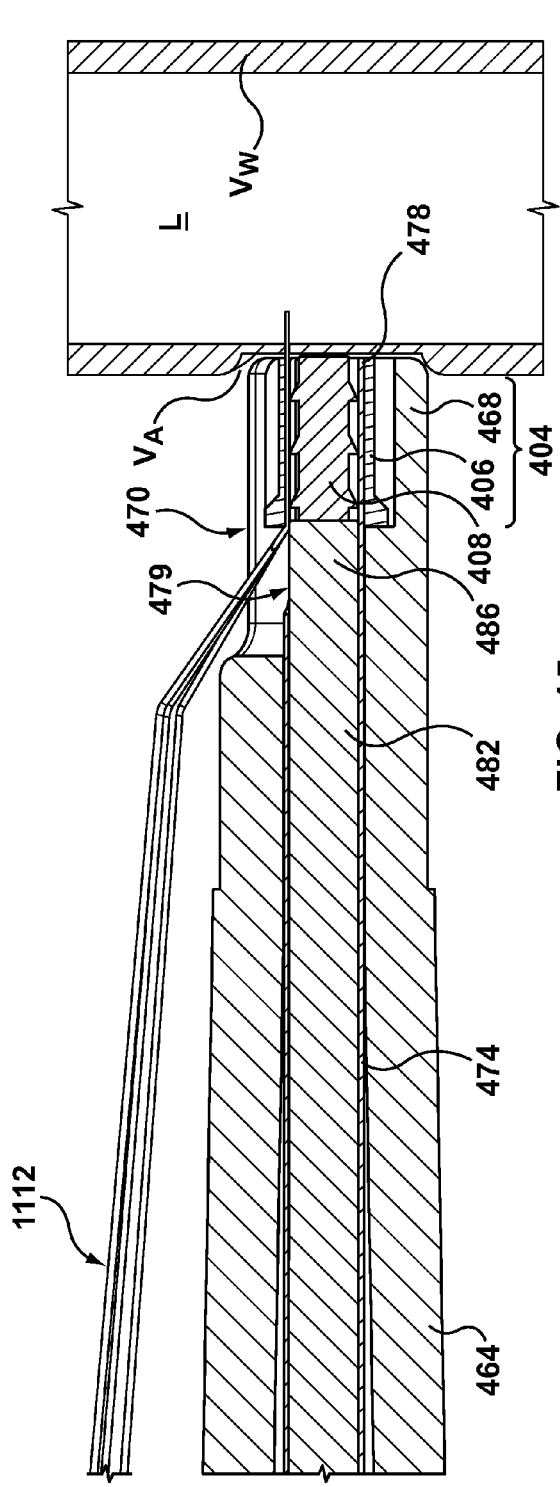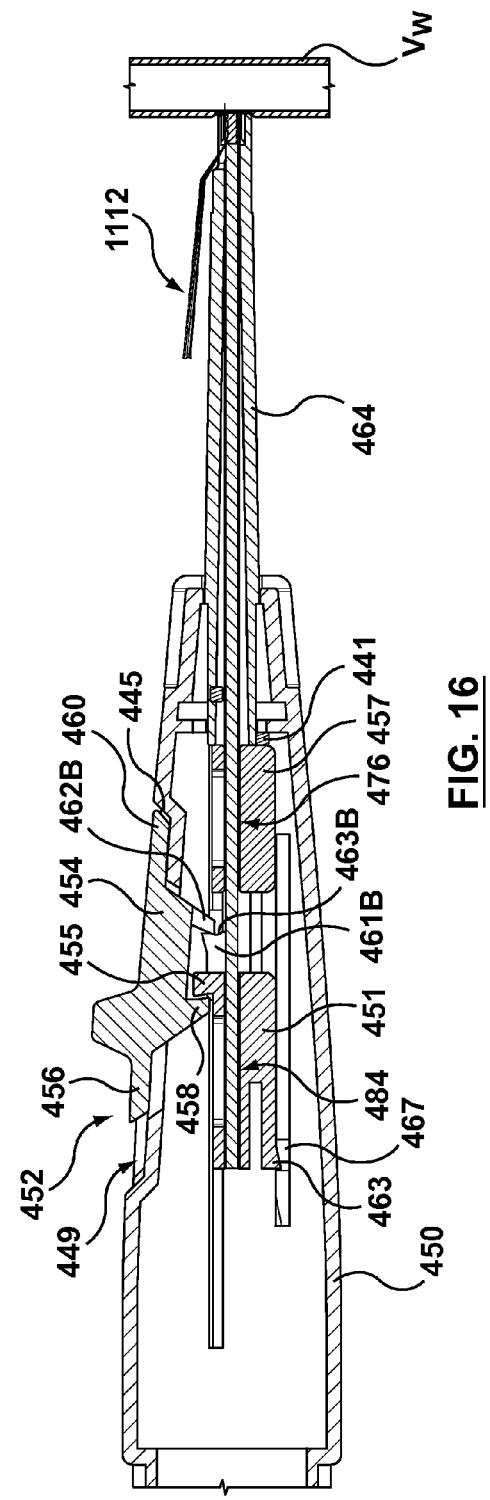

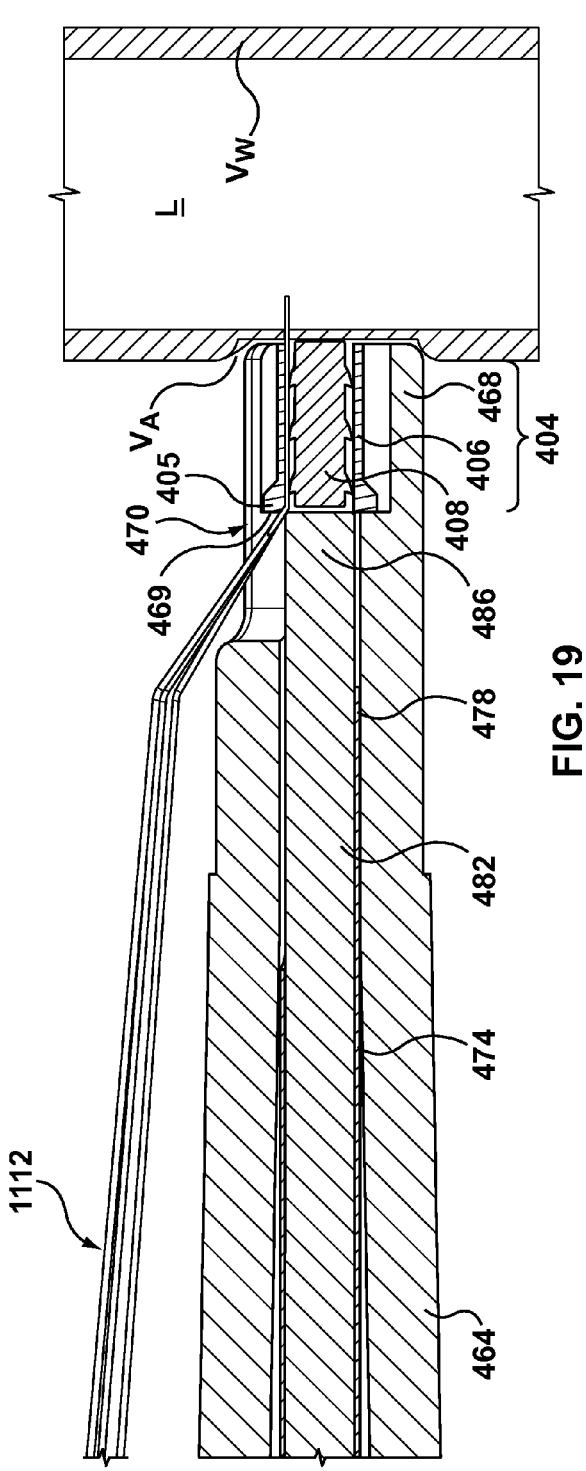
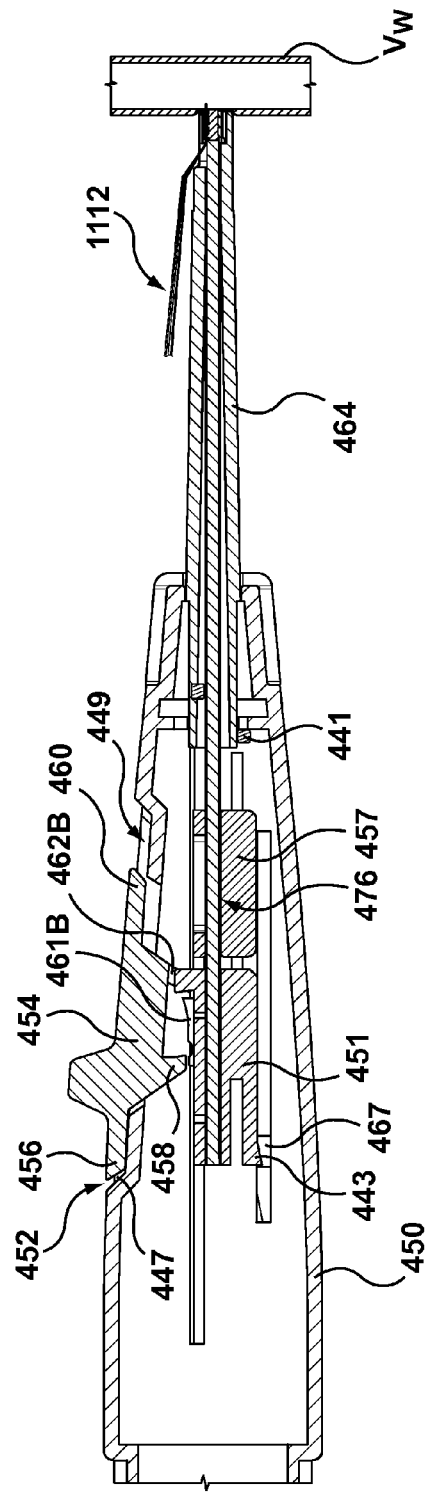

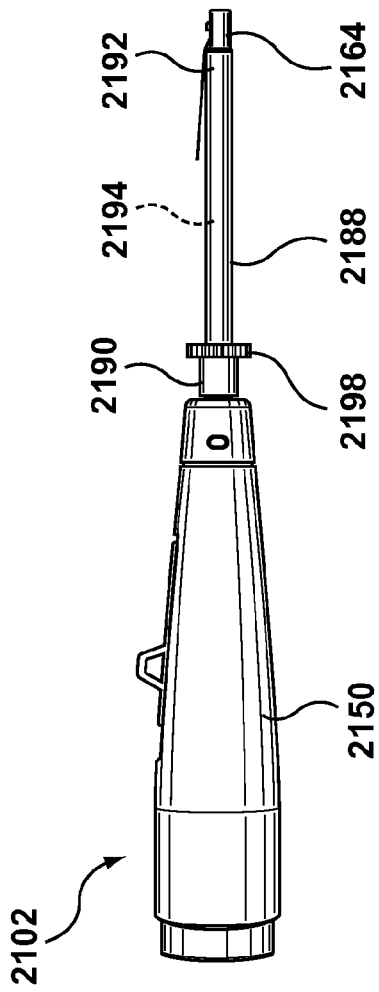
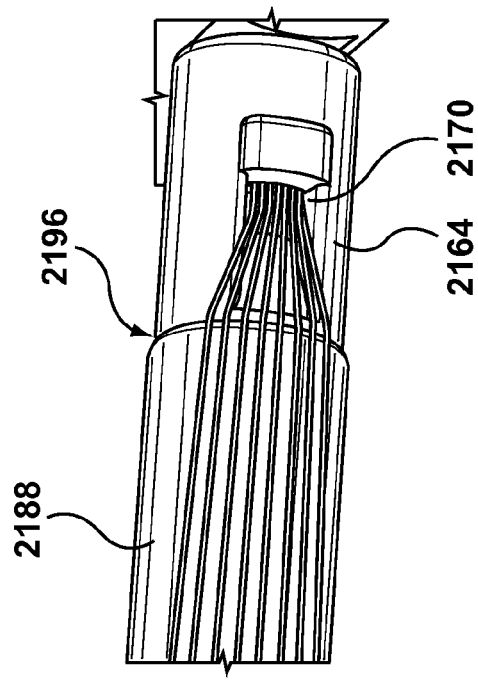
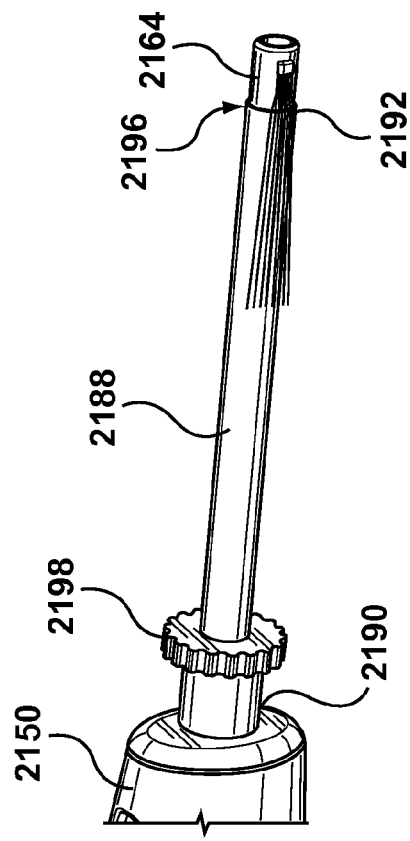
FIG. 21
FIG. 23
FIG. 22

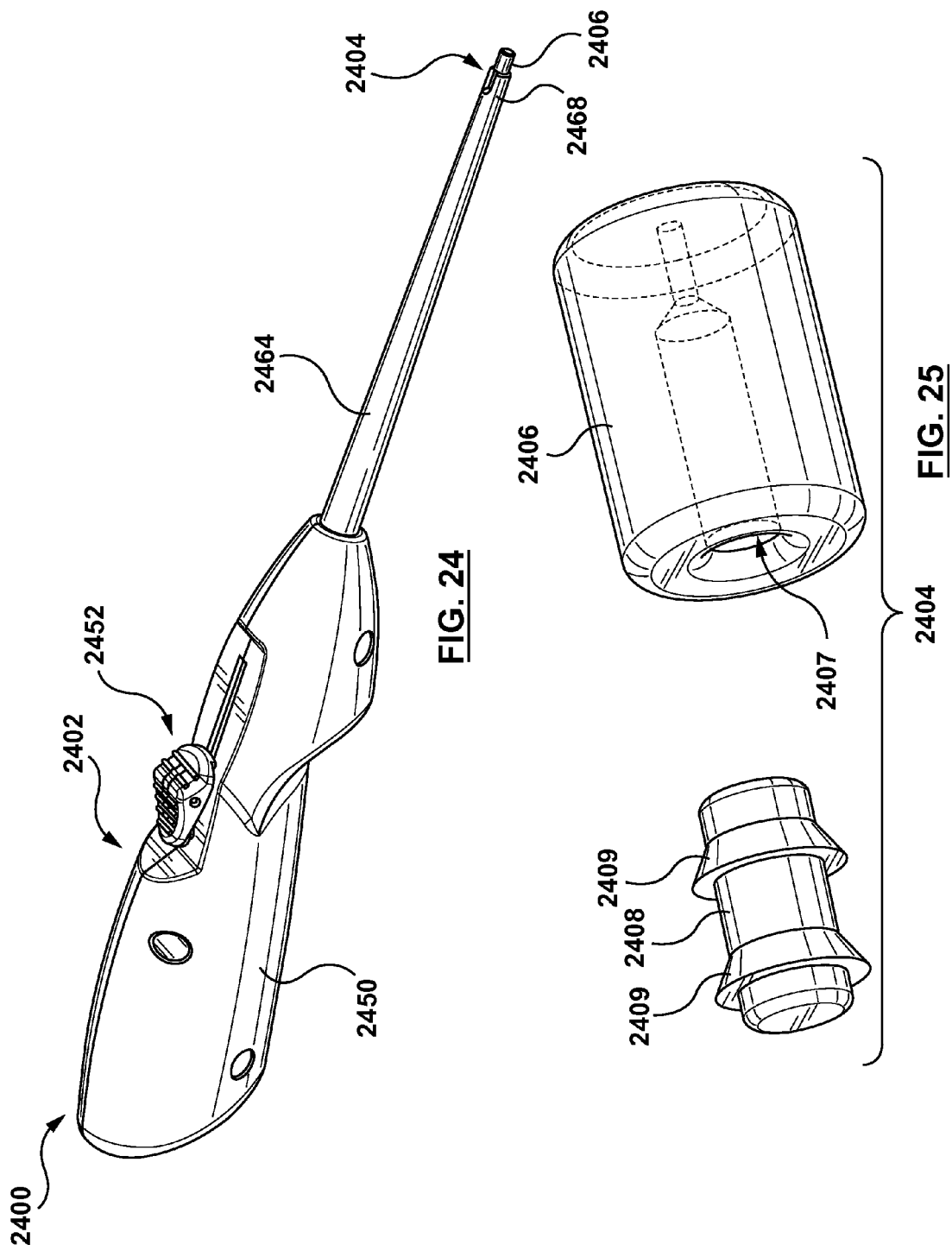

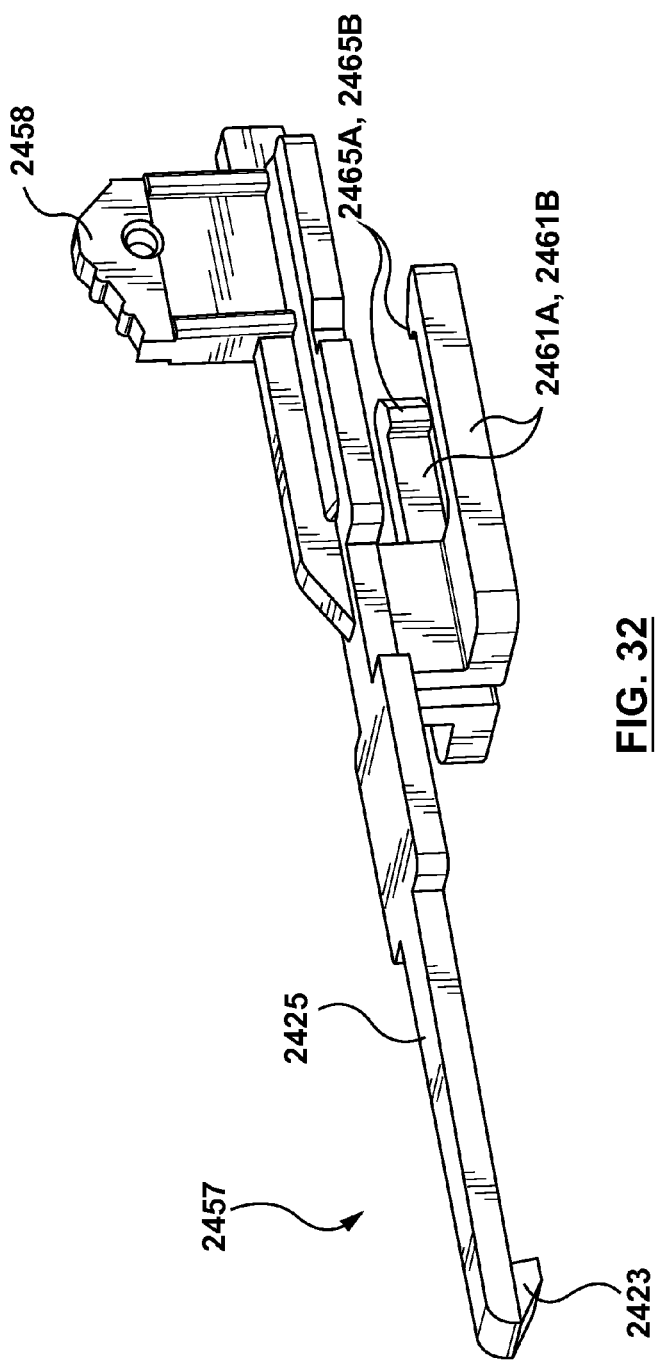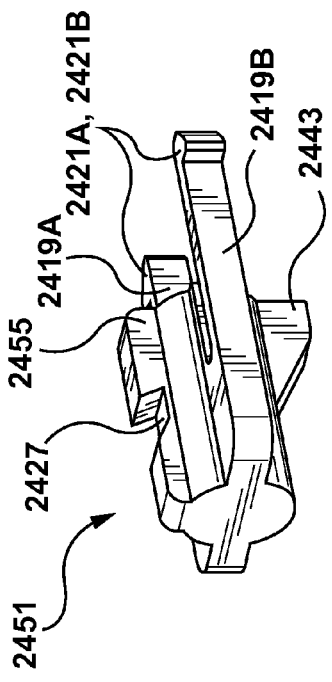

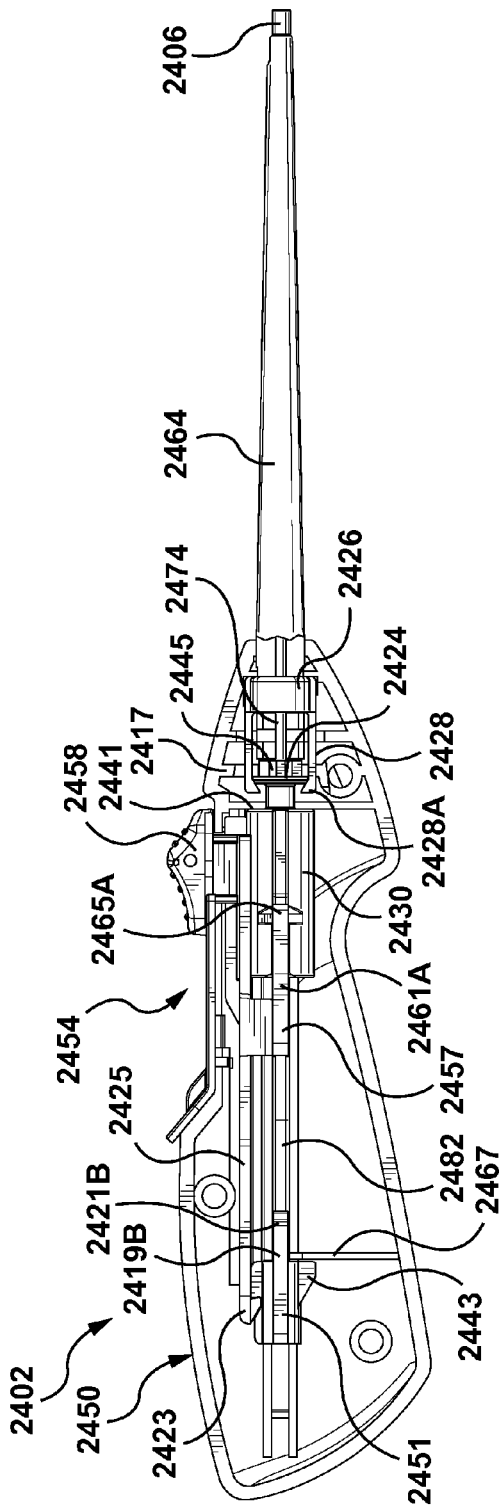
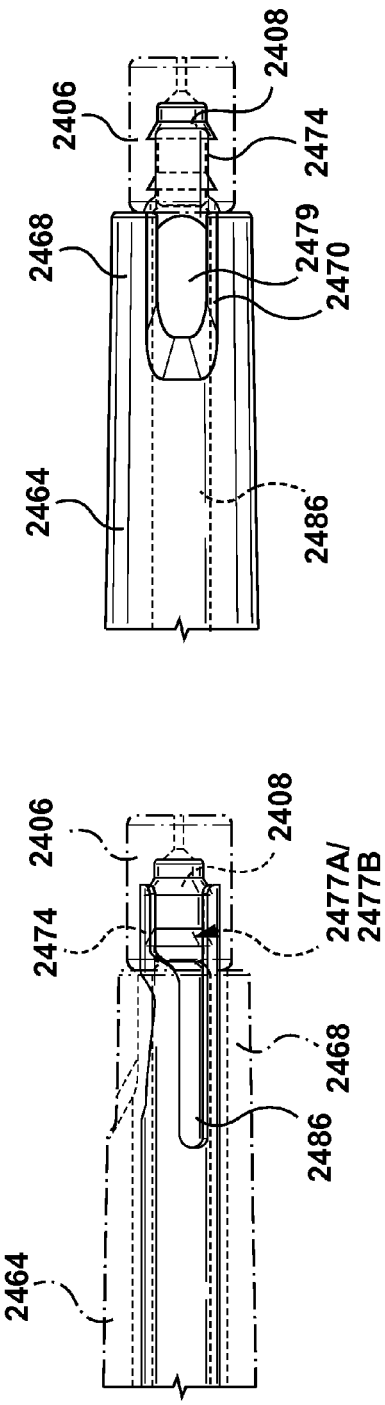
FIG. 34
FIG. 36
FIG. 35

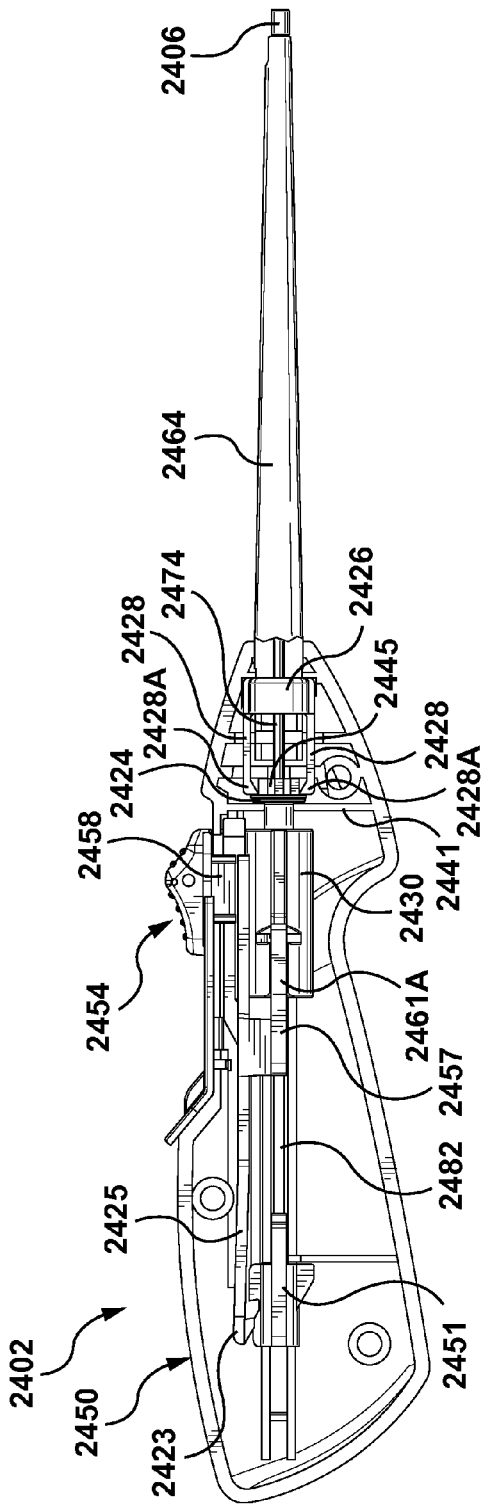
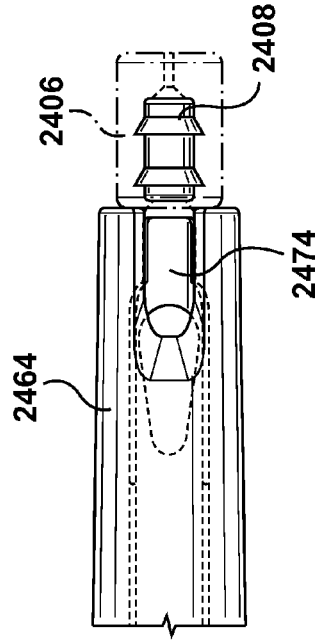
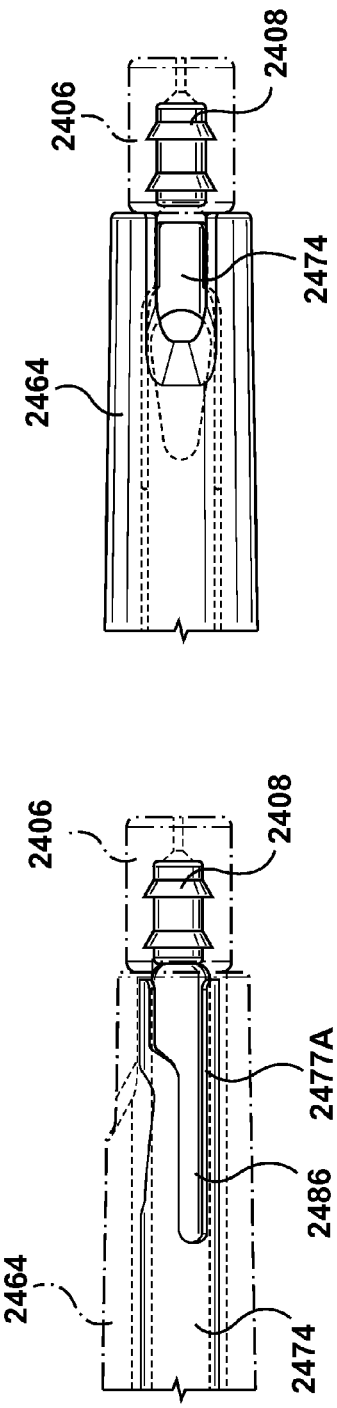
FIG. 37
FIG. 39
FIG. 38

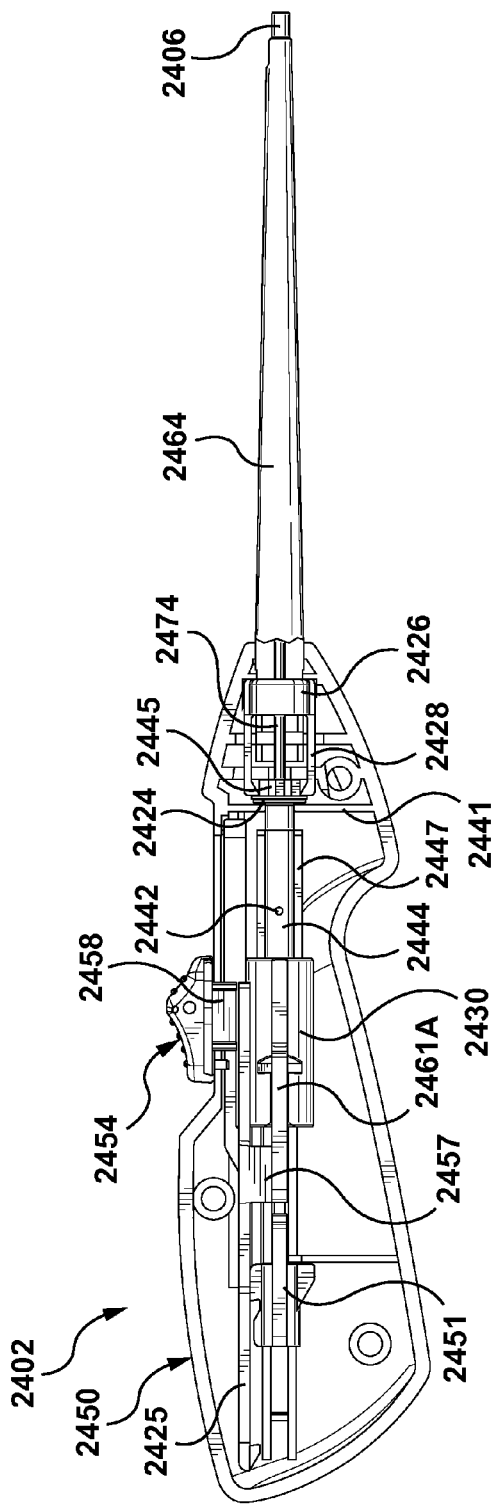
FIG. 40
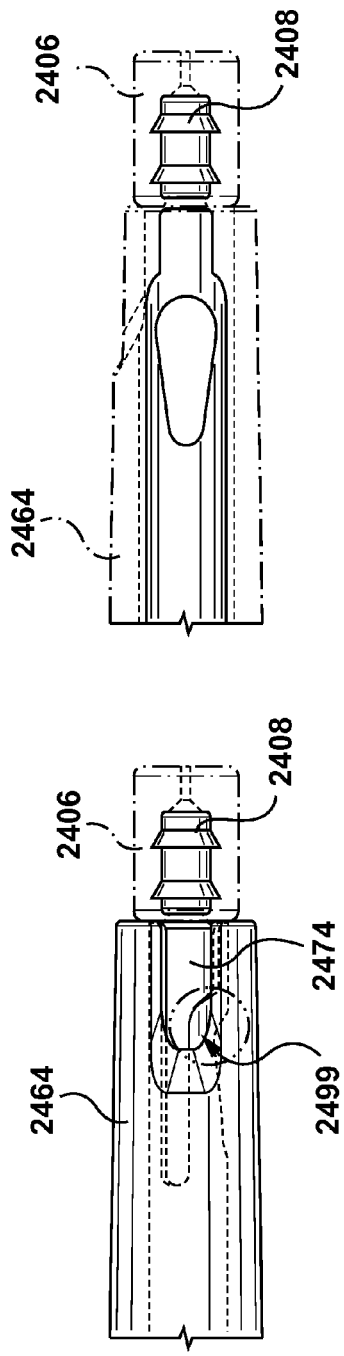
FIG. 42
FIG. 41

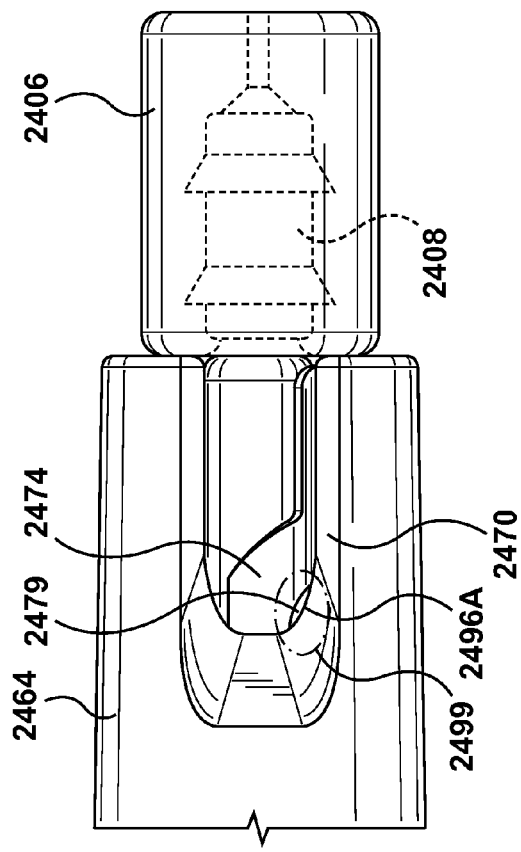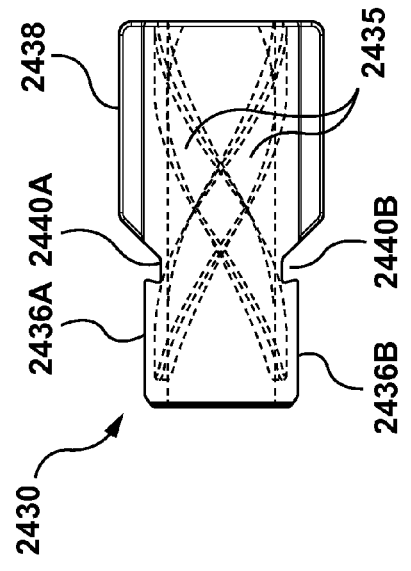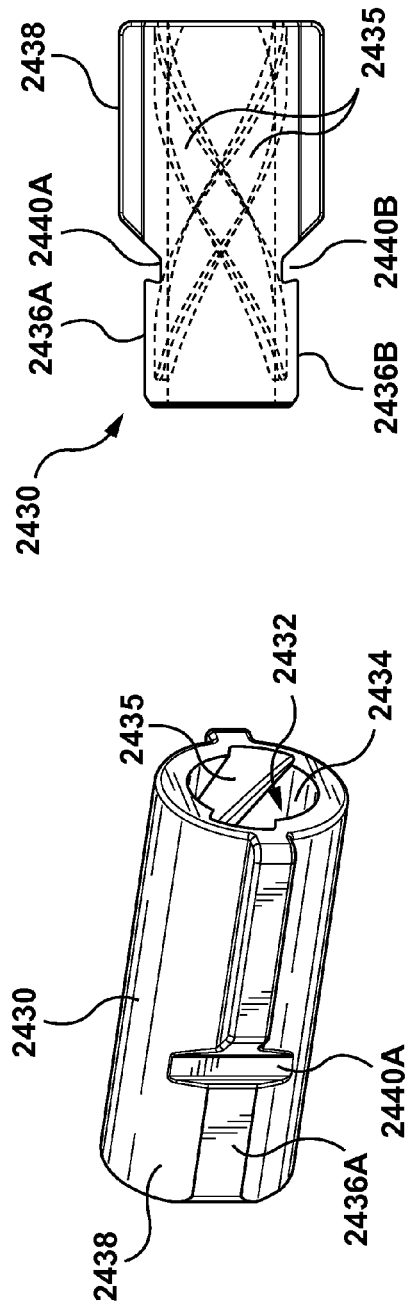

METHOD AND APPARATUS FOR FORMING
A SUTURE CONNECTOR IN SITU

CROSS-REFERENCE TO RELATED
APPLICATIONS

This application claims the benefit of U.S. patent application Ser. No. 14/180,016, filed Feb. 13, 2014, which is hereby incorporated by reference in its entirety for all purposes.

FIELD OF THE INVENTION

Embodiments hereof relate to medical suturing devices. More particularly, embodiments hereof relate to devices and methods for securing suture portions extending from an opening in an arterial or other biological tissue wall that is not directly accessible to the physician.

BACKGROUND OF THE INVENTION

Various cardiovascular procedures, such as angioplasty, stent placement and atherectomy, require gaining access to the vasculature. With reference to FIGS. 1 and 2, access to the vasculature of a patient typically is through the femoral artery and is percutaneous, involving insertion of a needle (not shown), and in some cases a dilator (not shown), in the region of the groin to form a track 103 through subcutaneous tissue T and to puncture and create an arteriotomy $V_A$ in a vessel wall $V_W$ of the femoral artery. A guidewire GW is then advanced through the needle and into the femoral artery. The needle and dilator, if present, are then removed. An introducer sheath 101, which is typically a single lumen catheter with a hemostasis valve on its proximal end, or other interventional device is then advanced over the guidewire GW, along the track 103 and into the femoral artery in order to perform the selected procedure. Introducer sheath 101 provides access into the femoral artery, through the arteriotomy, for longer guidewires, catheters or other instrumentalities in order to perform the selected procedure. The hemostasis valve on the introducer sheath is used to prevent extraneous bleed back or to introduce medication into the patient's body.

After the procedure has been completed, the interventional devices are removed and the arteriotomy must be closed. The size of the puncture opening in the artery corresponds to the size of the catheter or percutaneous introducer sheath used, and such devices may typically range in diameter from 5 French for a diagnostic procedure to 6-20 French for a therapeutic procedure. A number of techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain lying down, essentially motionless and often with a heavy sandbag placed on their upper leg, for several hours to ensure that the bleeding has stopped. The recovery time from the medical procedure may be as little as half of an hour, but the recovery time from the wound can exceed twenty-four hours. Longer recovery times may result in increased expenses, increased patient discomfort, and greater risk of complications. Other approaches to arteriotomy closure include a compression clamp device, a thrombotic or collagen plug, biological adhesives adapted to seal the arteriotomy, and/or stapling devices.

In addition, medical suturing systems have been proposed to facilitate closure and healing of the arteriotomy and resolve some of the concerns associated with arteriotomy closure after vascular catheterization procedures. In addition, beyond suturing devices utilized for closing arteriotomies, surgeons frequently encounter the need to close internal incisions, wounds, or otherwise joining tissue portions with a suture in situ. For example, FIG. 3 illustrates an incision 310 in the patient's skin used to perform a percutaneous or minimally invasive treatment on the patient. After the patient has been treated, a suture 312 is introduced into the patient through an introducer sheath 301 for the purpose of drawing together tissue portions 316, 318 (shown in phantom in FIG. 3). Two end portions 320, 322 of suture 312 extend from the tissue portions 316, 318, respectively, which may, for example, be the result of an internal wound or an arteriotomy in a blood vessel or an organ. Suture 312 may be introduced into the patient and positioned through tissue portions 316, 318 by any suitable manner or device, including but not limited to those described in U.S. Pat. No. 6,117,144 to Nobles et al., U.S. Pat. No. 6,562,052 to Nobles et al., U.S. Pat. No. 7,803,167 to Nobles et al., U.S. application Ser. No. 13/802,551 to Argentine, filed Mar. 13, 2013, and U.S. application Ser. No. 13/802,563 to Argentine, filed Mar. 13, 2013, all of which are hereby incorporated by reference in their entirety. Suture 312 is shown in FIG. 3 extending from catheter sheath introducer 301, but may alternatively extend directly from incision 310 in the patient.

After passing suture 312 through the tissue portions, i.e., after the suture has been positioned adjacent to the internal wound or arteriotomy, the two end portions 320, 322 of suture 312 must be tied or otherwise coupled together to draw the tissue portions together and prevent them from separating. The two end portions 320, 322 may be manually tied by the surgeon. However, sutures can often be difficult to handle and/or access, thereby increasing the procedure time. Thus, in some instances, surgeons prefer to use a device that secures or couples the two end portions of a suture in situ. For example, U.S. Pat. Nos. 8,197,497 and 8,469,975 to Nobles et al., which are assigned to the same assignee as the present application and are herein incorporated by reference in their entirety, describes a knot placement device that positions a knot or connector that secures or couples the two end portions of a suture in situ. The knot includes a knot body and a plug, and the knot placement device pushes a plug distally into the knot body and traps at least two suture portions between the plug and the knot body. The knot, i.e., the knot body and the plug, having the suture portions trapped therein may then be ejected out of the knot placement device. When ejected out of the knot placement device, the knot may be inadvertently pushed through the opening or arteriotomy of the treatment site. In addition to possibly losing or reducing hemostasis, if inadvertently pushed through the arteriotomy, the knot may contact and damage the inner vessel wall opposite the incision/arteriotomy.

Embodiments hereof relate to improvements of a device that secures or couples two or more suture portions.

BRIEF SUMMARY OF THE INVENTION

Embodiments hereof relate to a system for forming a suture connector in situ including a suture connector placement device and a suture connector. The suture connector placement device includes a handle having an actuating mechanism, an outer shaft, an intermediate shaft, and a push rod. The outer shaft defines a lumen from a proximal end to a distal end thereof. The proximal end of the outer shaft is coupled to the handle and the outer shaft includes a side opening adjacent to the distal end thereof. The intermediate shaft defines a lumen from a proximal end to a distal end thereof. The intermediate shaft is slidingly disposed within the lumen of the outer shaft with the proximal end of the intermediate shaft being coupled to the actuating mechanism of the handle. The push rod is slidingly disposed within the lumen of the intermediate shaft. The proximal end of the push rod is coupled to the actuating mechanism of the handle. The suture connector includes a sleeve and a plug. When the suture connector is in a loaded configuration, the sleeve of the suture connector is disposed on an outer surface of the intermediate shaft via an interference fit there-between and extends from the distal end of the outer shaft and the plug of the suture connector is slidably disposed within the lumen of the intermediate shaft proximal of the sleeve.

Embodiments hereof also relate to a system for forming a suture connector in situ including a suture connector placement device and a suture connector. The suture connector placement device includes a handle having an actuating mechanism, an outer shaft, an intermediate shaft, and a push rod. The outer shaft defines a lumen from a proximal end to a distal end thereof. The proximal end of the outer shaft is coupled to the handle and the outer shaft includes a side opening adjacent to the distal end thereof. The intermediate shaft defines a lumen from a proximal end to a distal end thereof. The intermediate shaft is slidingly disposed within the lumen of the outer shaft with the proximal end of the intermediate shaft being coupled to the actuating mechanism of the handle, which is configured to proximally retract the intermediate shaft. The intermediate shaft includes a plurality of side openings, each side opening being of a pre-formed width and extending in a proximal direction from the distal end of the intermediate shaft. The push rod is slidingly disposed within the lumen of the intermediate shaft. The proximal end of the push rod is coupled to the actuating mechanism of the handle, which is configured to distally advance the push rod. The suture connector includes a sleeve formed of a resilient material and a plug. When the suture connector is in a loaded configuration, the sleeve of the suture connector is disposed on an outer surface of the intermediate shaft over the plurality of side openings thereof, thereby compressing the plurality of side openings of the intermediate shaft and reducing their pre-formed widths and the plug of the suture connector is slidably disposed within the lumen of the intermediate shaft proximal of the sleeve. Distal advancement of the push rod moves the plug to longitudinally position the plug within the sleeve, thereby expanding the plurality of side openings of the intermediate shaft to return to their pre-formed widths. Proximal retraction of the intermediate shaft releases the sleeve onto the plug.

Embodiments hereof also relate to a system for forming a suture connector in situ including a suture connector placement device and a suture connector. The suture connector placement device includes a handle having an actuating mechanism, an outer shaft, an intermediate shaft, and a push rod. The outer shaft defines a lumen from a proximal end to a distal end thereof. The proximal end of the outer shaft is coupled to the handle and the outer shaft includes a side opening adjacent to the distal end thereof. The intermediate shaft defines a lumen from a proximal end to a distal end thereof. The intermediate shaft is slidingly and rotatably disposed within the lumen of the outer shaft with the proximal end of the intermediate shaft being coupled to the actuating mechanism of the handle. The intermediate shaft includes a window adjacent to the distal end thereof, and the window of the intermediate shaft includes a cutting surface operable to sever the at least one suture portion. The push rod is slidingly disposed within the lumen of the intermediate shaft. The proximal end of the push rod is coupled to the actuating mechanism of the handle. The suture connector includes a sleeve and a plug. When the suture connector is in a loaded configuration, the sleeve of the suture connector is disposed on an outer surface of the intermediate shaft and the plug of the suture connector is slidably disposed within the lumen of the intermediate shaft proximal of the sleeve.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 6 is a sectional view of a system of the suture connector of FIG. 5 positioned within a distal portion of the suture connector placement device of FIG. 4, wherein the suture connector is in a loaded or delivery configuration within the suture connector placement device.

FIG. 6A is a cross-sectional view of FIG. 6 taken along line A-A of FIG. 6.

FIG. 11 is an enlarged side sectional view of a distal end of the suture connector placement device of FIG. 4 abutting against tissue having an arteriotomy $V_A$ in the vessel wall $V_W$ of a vessel, wherein the suture connector is in a loaded or delivery configuration within the suture connector placement device.

FIG. 12 is a side sectional view of the suture connector placement device of FIG. 4 abutting against tissue having an arteriotomy $V_A$ in the vessel wall $V_W$ of a vessel, wherein the suture connector is in a loaded or delivery configuration within the suture connector placement device.

FIG. 13 is an enlarged side sectional view of a distal end of the suture connector placement device of FIG. 4 abutting against tissue having an arteriotomy $V_A$ in the vessel wall $V_W$ of a vessel, wherein a push rod of the suture connector placement device is shown advancing the plug towards the sleeve.

FIG. 14 is a side sectional view of the suture connector placement device of FIG. 4 abutting against tissue having an arteriotomy $V_A$ in the vessel wall $V_W$ of a vessel, wherein a push rod of the suture connector placement device is shown advancing the plug towards the sleeve.

FIG. 15 is an enlarged side sectional view of a distal end of the suture connector placement device of FIG. 4 abutting against tissue having an arteriotomy $V_A$ in the vessel wall $V_W$ of a vessel, wherein the push rod of the suture connector placement device is in an extended position and the suture connector is in a pre-deployed configuration with the plug of the suture connector extended or relocated into the sleeve but not yet in contact with the sleeve.

FIG. 16 is a side sectional view of the suture connector placement device of FIG. 4 abutting against tissue having an arteriotomy $V_A$ in the vessel wall $V_W$ of a vessel, wherein the push rod of the suture connector placement device is in an extended position and the suture connector is in a pre-deployed configuration with the plug of the suture connector extended or relocated into the sleeve but not yet in contact with the sleeve.

FIG. 19 is an enlarged side sectional view of a distal end of the suture connector placement device of FIG. 4 abutting against tissue having an arteriotomy $V_A$ in the vessel wall $V_W$ of a vessel, wherein the intermediate shaft of the suture connector placement device is in a retracted position and the suture connector is in a fully deployed configuration with the plug of the suture connector in contact with the sleeve.

FIG. 20 is a side sectional view of the suture connector placement device of FIG. 4 abutting against tissue having an arteriotomy $V_A$ in the vessel wall $V_W$ of a vessel, wherein the intermediate shaft of the suture connector placement device is in a retracted position and the suture connector is in a fully deployed configuration with the plug of the suture connector in contact with the sleeve.

FIG. 21 is a side view of a suture connector placement device for positioning a suture connector in situ according to another embodiment hereof, wherein the suture connector placement device includes an outermost shaft having a cutting surface at its distal end.

FIG. 22 is a perspective view of a distal portion of the suture connector placement device of FIG. 21.

FIG. 23 is an enlarged view of a portion of FIG. 22.

FIG. 24 is a side view of a suture connector placement device for positioning a suture connector in situ according to another embodiment hereof, wherein an intermediate shaft thereof is rotatable for trimming sutures.

FIG. 25 is a side view of a suture connector to be used with the suture connector placement device of FIG. 24, wherein the suture connector includes a plug and a sleeve.

FIG. 32 is a perspective view of a second coupler of an actuating mechanism of the suture connector placement device of FIG. 24, wherein the second coupler is removed from a handle of the system for sake of illustration only.

FIG. 33 is a perspective view of a first coupler of an actuating mechanism of the suture connector placement device of FIG. 24, wherein the first coupler is removed from a handle of the system for sake of illustration only.

FIG. 34 is a sectional view of the suture connector placement device of FIG. 24, wherein a push rod of the suture connector placement device is in an extended position and the suture connector is in a pre-deployed configuration with the plug of the suture connector extended or relocated into the sleeve but not yet in contact with the sleeve.

FIG. 35 is an enlarged side view of a distal end of FIG. 34.

FIG. 36 is an enlarged side view of the distal end of FIG. 34, the side view being rotated ninety degrees relative to the side view of FIG. 35.

FIG. 37 is a sectional view of the suture connector placement device of FIG. 24, wherein the intermediate shaft of the suture connector placement device is in a retracted position and the suture connector is in a fully deployed configuration with the plug of the suture connector in contact with the sleeve.

FIG. 38 is an enlarged side view of a distal end of FIG. 37.

FIG. 39 is an enlarged side view of the distal end of FIG. 37, the side view being rotated ninety degrees relative to the side view of FIG. 38.

FIG. 40 is a sectional view of the suture connector placement device of FIG. 24, wherein the intermediate shaft has been rotated in order to trim the sutures and the suture connector is in a fully deployed configuration with the plug of the suture connector in contact with the sleeve.

FIG. 41 is an enlarged side view of a distal end of FIG. 40.

FIG. 42 is an enlarged side view of the distal end of FIG. 40, the side view being rotated ninety degrees relative to the side view of FIG. 41.

FIG. 43 is an enlarged view of FIG. 41.

FIG. 44 is a perspective view of a lead of the suture connector placement device of FIG. 24, wherein the lead is removed from a handle of the system for sake of illustration only.

FIG. 45 is a side view of the lead of FIG. 44.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Embodiments described below relate to a device for securing or coupling two suture portions extending from a treatment location of a patient, or otherwise stated for applying a connector to two suture portions extending from a treatment location of a patient. Suture portions may be portions of the same suture or may be portions of separate and different sutures. The treatment location may be any desired location, such as an arterial or venous blood vessel. Although the description of the invention is in the context of treatment of blood vessels, the invention may also be used in any other body passageways where it is deemed useful. For example, the device could be used to suture other tissue such as a patent ductus arteriosus, a patent foramen ovale, a heart defect, a puncture wound, and the like. There is no intention to be bound by any expressed or implied theory presented in the preceding technical field, background, brief summary or the following detailed description.

Figure 1:
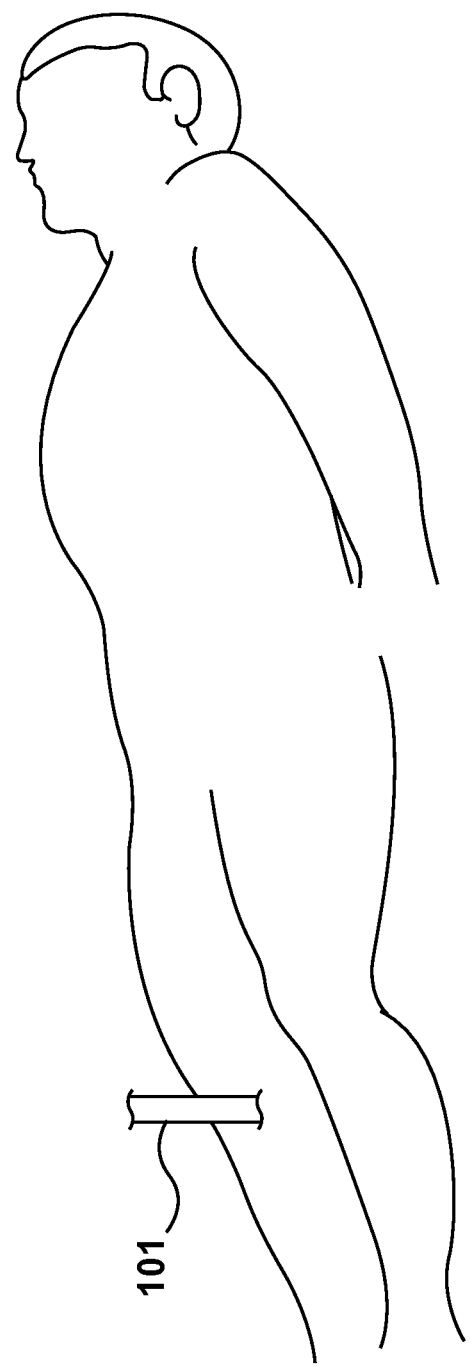
FIGS. 1 and 2 illustrate the introduction of an introducer sheath into the vasculature via the femoral artery, thereby forming an arteriotomy in a vessel wall of the femoral artery.
Figure 2:
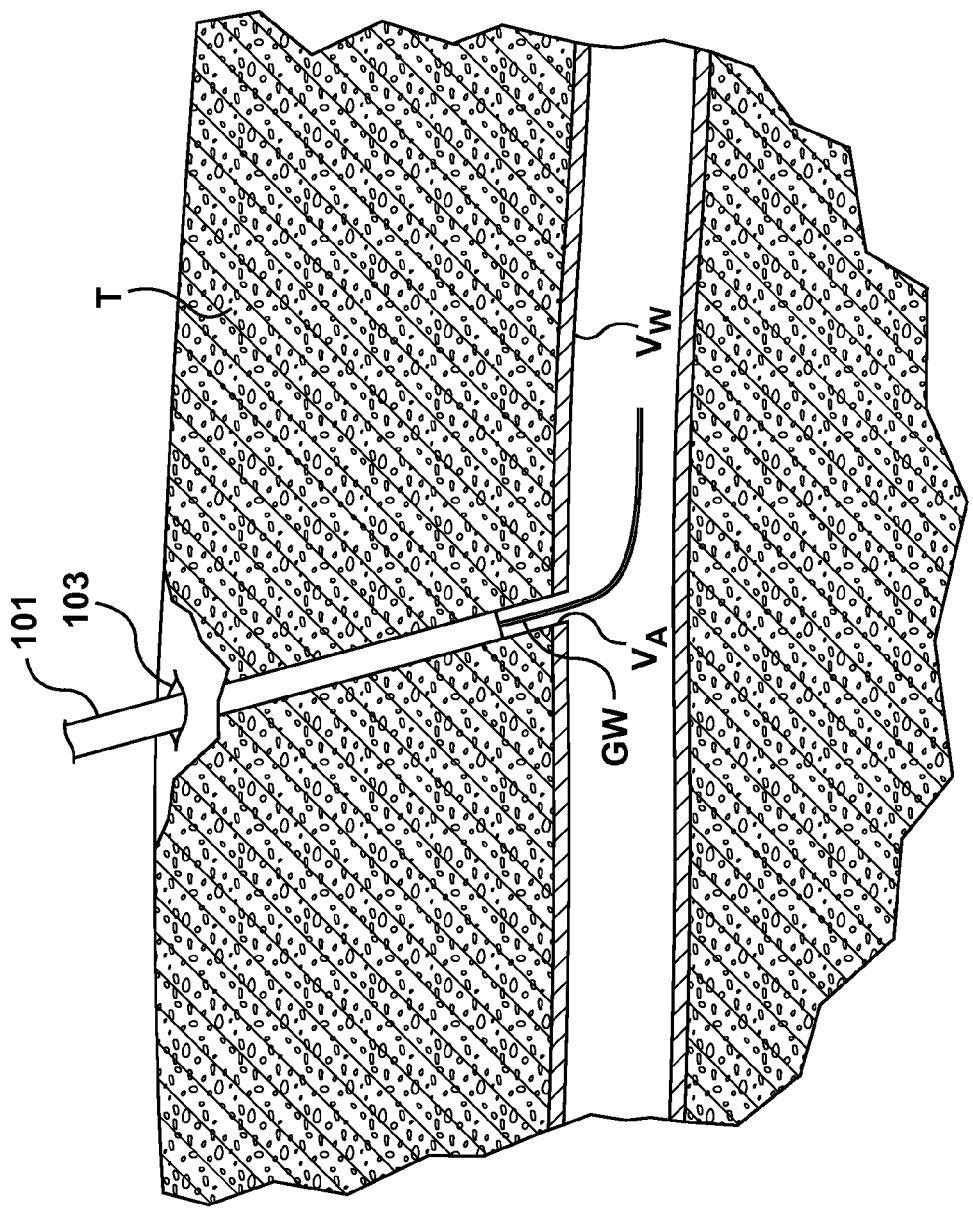
Figure 3:
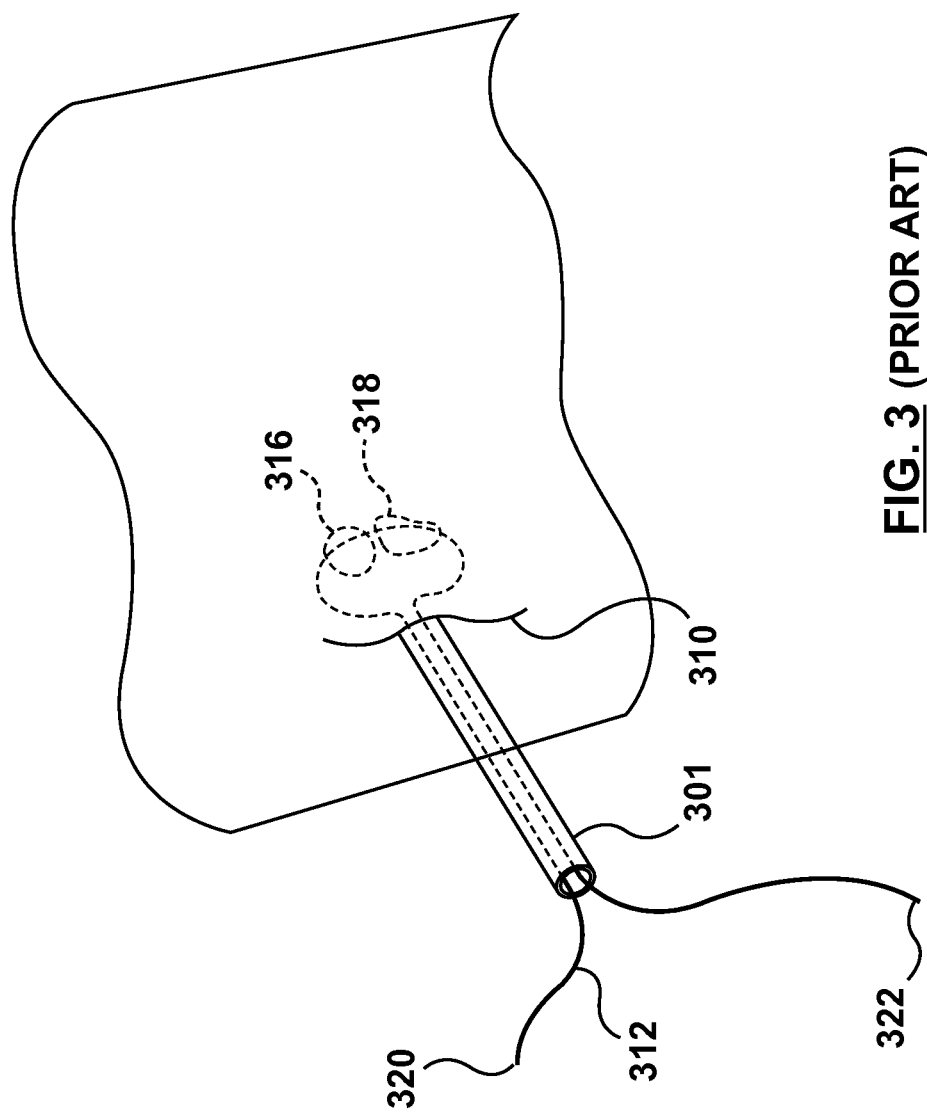
FIG. 3 is a perspective view of a wound site having a pair of suture ends extending therefrom.
Figure 4:
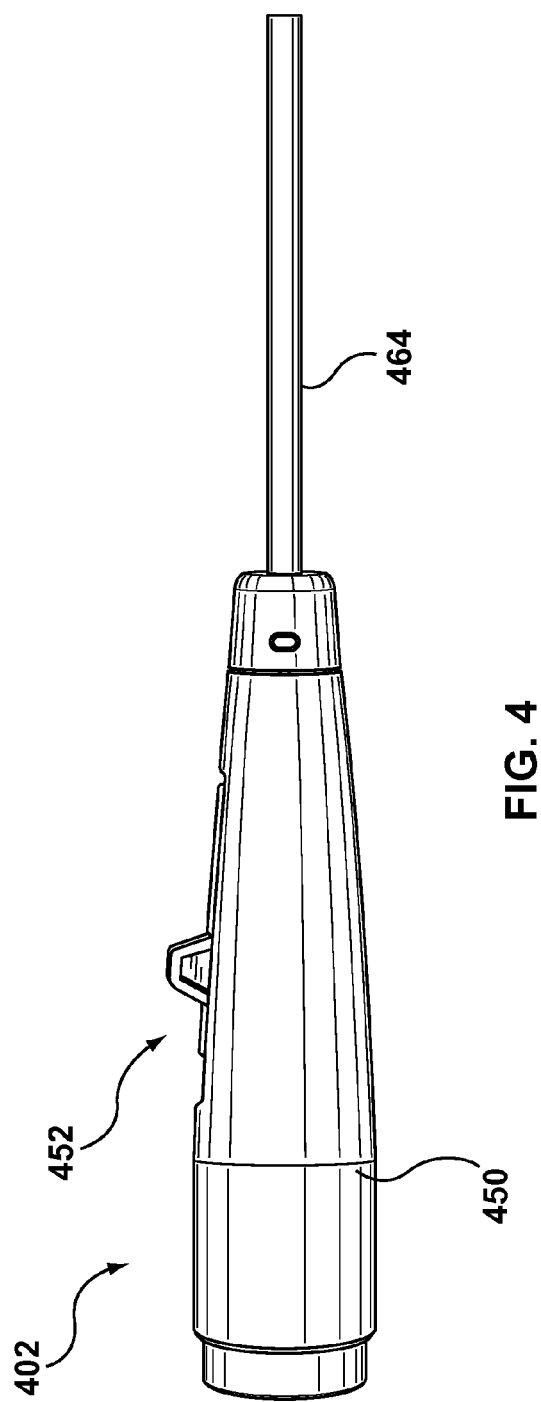
FIG. 4 is a side view of a suture connector placement device for positioning a suture connector in situ according to an embodiment hereof.
Figure 5:
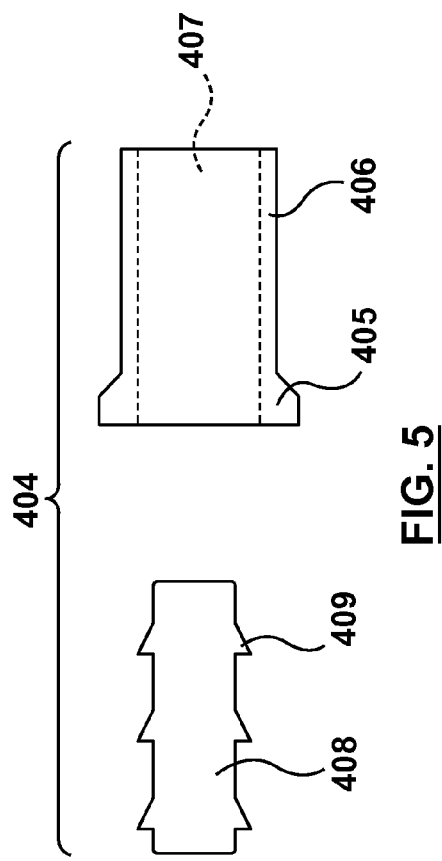
FIG. 5 is a side view of a suture connector to be used with the suture connector placement device of FIG. 4, wherein the suture connector includes a plug and a sleeve.

FIG. 4 illustrates a side view of a suture connector placement device 402 for positioning a knot or suture connector 404 in situ, while FIG. 5 is a side view of suture connector 404. Collectively, suture connector placement device 402 and suture connector 404 may be considered a system 400 for forming a suture connector in situ. Suture connector placement device 402 includes a handle 450 having an actuating mechanism 452 therein and an outer shaft 464 distally extending from handle 450. Suture connector 404 includes a cylindrical component or plug 408 and a tubular component or sleeve 406 which defines a lumen 407 there-through. Sleeve 406 includes a circumferential flange 405 radially extending from its outer surface. Flange 405 functions to interact with suture connector placement device 402 during operation thereof, as will be described in more detail herein. Plug 408 has an outer dimension and a length configured to be inserted into the lumen 407 of sleeve 406. Plug 408 may include radial protrusions 409 extending from its outer surface to ensure an interference or press fit between plug 408 and sleeve 406 when the plug and the sleeve are assembled or joined as will be described in more detail herein. Protrusions 409 may be rings, spirals, spikes, bumps, or other suitable structures. When loaded into suture connector placement device 402, as will be explained in more detail below, sleeve 406 and plug 408 are disposed within a distal end of the device such that plug 408 is positioned proximal of sleeve 406. Operation of suture connector placement device 402 to fully deploy and form suture connector 404 in situ may be considered a two-stage or two-step deployment process. In a first step or stage of the deployment operation that will be described in more detail herein, suture connector placement device 402 causes plug 408 to be distally advanced or pushed into sleeve 406, although sleeve 406 and plug 408 are not yet in contact with each other at this stage of deployment. Once the sleeve and plug are longitudinally aligned with each other, suture connector 404 is in a pre-deployed configuration. In a second step or stage of the deployment operation that will be described in more detail herein, suture connector placement device 402 causes sleeve 406 to be released onto plug 408, thereby securing or clamping suture portions (not shown in FIGS. 4-5) between the plug and the sleeve to thereby secure or hold the suture portions together relative to each other within the formed connector. The suture portions are secured or coupled together via the interference or press fit between plug 408 and sleeve 406. Once the sleeve is released onto the plug, suture connector 404 is formed and in a fully deployed configuration. Suture connector 404 may be used to secure suture portions that are positioned adjacent to an opening or arteriotomy of a blood vessel or other biological tissue following an interventional catheterization procedure, thereby closing or sealing the opening or arteriotomy to achieve hemostasis.

Correct positioning of suture connector 404 is essential for achieving closure of the opening or arteriotomy and hemostasis at the treatment site. In order to ensure that suture connector 404 is correctly positioned at a treatment site and hemostasis occurs, suture connector placement device 402 is designed such that outer shaft 464 abuts against tissue of the treatment site, with the distal end thereof disposed over or covering the opening or arteriotomy of the treatment site, and is designed such that suture connector 404 is not pushed or ejected out of the device after plug 408 is positioned within sleeve 406. Such a design ensures that suture connector 404 is correctly positioned against tissue of the treatment site and is not inadvertently pushed through the opening or arteriotomy of the treatment site. In addition, suture connector placement device 402 is designed to permit adjustment of suture portions after plug 408 is positioned within sleeve 406. Rather than locking or clamping suture portions in between the plug and sleeve as soon as the device has been fired or deployed, the two-stage deployment operation of system 400 permits a user to pull or tighten the suture portions if needed after plug 408 is positioned into sleeve 406, i.e., after suture connector 404 has been pre-deployed, in order to ensure that hemostasis is achieved at the treatment site. Additional advantages or improvements of suture connector placement device 402 and connector 400 are discussed herein with reference to the figures.

Figure 7:
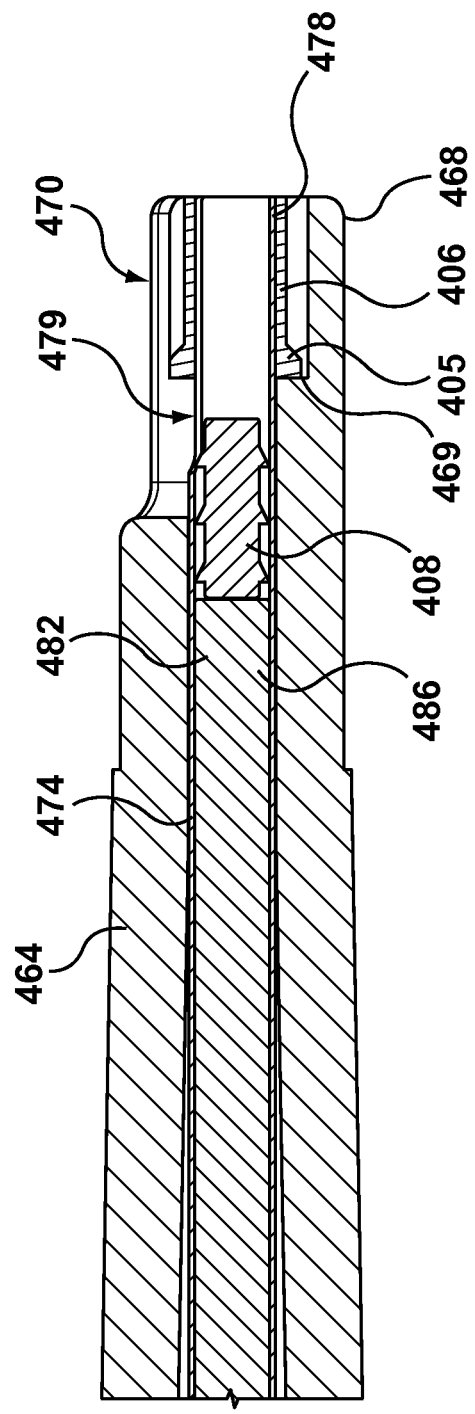
FIG. 7 is an enlarged view of a distal portion of FIG. 6.

The components of suture connector placement device 402 will now be described with reference to FIGS. 6, 6A, and 7. FIG. 6 is a sectional view of FIG. 4, FIG. 6A is a cross-sectional view taken along line A-A of FIG. 6, and FIG. 7 is an enlarged view of the distal end portion of FIG. 6. Suture connector placement device 402 includes outer shaft 464, an intermediate shaft 474, a push rod 482, and handle 450 having actuating mechanism 452 which includes a slider 454, a first coupler 451, and a second coupler 457. These components of suture connector placement device 402 may be made of any suitable material, including but not limited to metals, plastics, and a combination of metals and plastics. As best shown in FIG. 6A, intermediate shaft 474 is slidingly disposed through a lumen 472 of outer shaft 464, and push rod 482 is slidingly disposed through a lumen 480 of intermediate shaft 474. Outer shaft 464 is an elongate tubular component defining lumen 472 and has a proximal end 466 that extends into and is coupled to handle 450. A distal end 468 of outer shaft 464 is sized and configured to abut against an outer surface of a vessel wall or other body tissue. Distal end 468 is of sufficient size to be disposed over or cover the opening or arteriotomy of the treatment site. For example, the outer diameter of distal end 468 of outer shaft 464 may be between 15 and 20 French. Outer shaft 464 also includes a side opening or port 470 proximal to its distal end 468. Adjacent to distal end 468 of outer shaft 464, a distal portion of lumen 472 has a greater or larger diameter than the remaining proximal length thereof in order to create an abutment surface 469 along the inner surface of outer shaft 464. As will be explained in more detail herein, abutment surface 469 functions to hold sleeve 406 stationary when intermediate shaft 474 is retracted.

Intermediate shaft 474 is a tubular component defining lumen 480 and has a proximal end 476 that extends into and is attached to second coupler 457 of actuating mechanism 452, as will be explained in more detail herein. A distal end 478 of intermediate shaft 474 extends to distal end 468 of outer shaft 464. Intermediate shaft 474 also includes a side opening or port 479 proximal to its distal end 478. Since intermediate shaft 474 is retracted during operation of suture connector placement device 402 as will be described in more detail herein, in one embodiment, side port 479 extends to its distal end 478 to ensure alignment of side port 479 of intermediate shaft 474 and side port 470 of outer shaft 464 during device operation. As shown in the enlarged view of FIG. 7, sleeve 406 of suture connector 404 is disposed on an outer surface of intermediate shaft 474 within lumen 472 of outer shaft 464 adjacent to distal end 468 of the outer shaft when suture connector 404 is in a loaded configuration within suture connector placement device 402 as described in more detail with reference to FIGS. 11 and 12. Plug 408 of suture connector 404 is slidingly disposed within intermediate shaft 474, proximal to sleeve 406, when suture connector 404 is in a loaded configuration within suture connector placement device 402 as described in more detail with reference to FIGS. 11 and 12.

Push rod 482 is a solid cylindrical component and has a proximal end 484 that extends into and is attached to first coupler 451 of actuating mechanism 452, as will be explained in more detail herein. As shown in the enlarged view of FIG. 7, a distal end 486 of push rod 482 is positioned or disposed proximal to a proximal end of plug 408 when suture connector 404 is in a loaded configuration within suture connector placement device 402 as described in more detail with reference to FIGS. 11 and 12.

Figure 8:
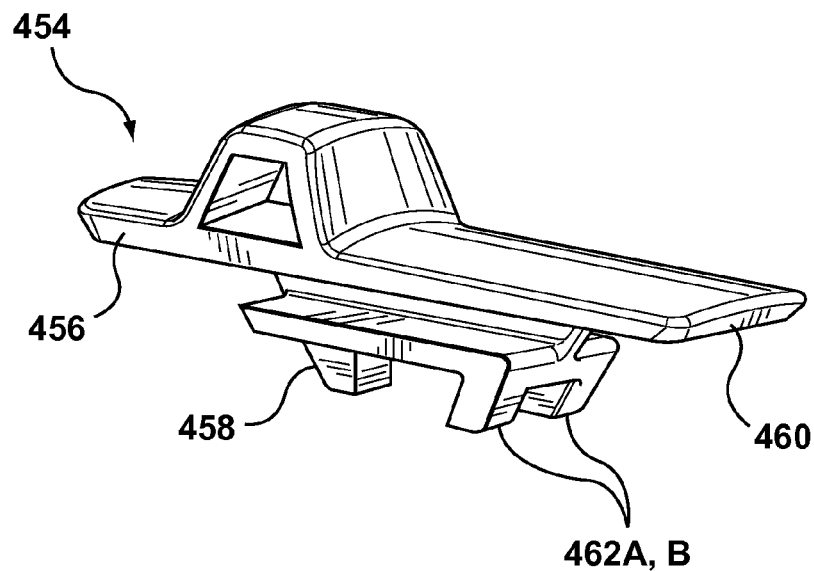
FIG. 8 is a perspective view of a slider of an actuating mechanism of the system of FIG. 6, wherein the slider is removed from a handle of the system for sake of illustration only.
Figure 9:
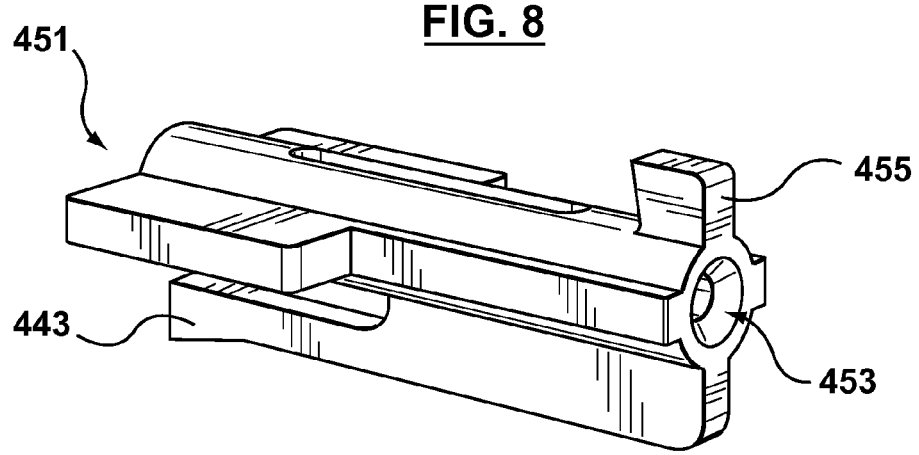
FIG. 9 is a perspective view of a first coupler of an actuating mechanism of the system of FIG. 6, wherein the first coupler is removed from a handle of the system for sake of illustration only.

Actuating mechanism 452 includes slider 454, first coupler 451 that couples proximal end 484 of push rod 482 to slider 454, and second coupler 457 that couples proximal end 476 of intermediate shaft 474 to slider 454. Actuating mechanism 452 is configured to distally advance push rod 482 via interaction between slider 454 and first coupler 451, and is also configured to proximally retract intermediate shaft 474 via interaction between slider 454 and second coupler 457. Advantageously, from a user perspective, operation of actuating mechanism 452 requires interaction with only slider 454, with distal advancement of slider 454 being employed in the first step or stage of deployment to push plug 408 into sleeve 406 and proximal retraction of slider 454 being employed in the second step or stage of deployment to retract intermediate shaft 474 and thereby release sleeve 406 onto plug 408. More particularly, slider 454 is housed within a recess 449 of the handle such that a top surface thereof is accessible to the user and a bottom or underside surface interacts with the remaining components of actuating mechanism 452. With additional reference to FIG. 8, slider 454 includes a proximal end 456 having a first knob or boss 458 on an underside surface thereof and a distal end 460 having a pair of spaced-apart knobs or bosses 462A, 462B on the underside surface thereof. With additional reference to FIG. 9, first coupler 451 includes a lumen 453 through at least a distal portion thereof for receiving proximal end 484 of push rod 482. First coupler 451 also includes a knob or boss 455 at its distal end that extends in an upward direction towards slider 454 for interaction or engagement with first knob 458 of slider 454, and a dovetail 443 at its proximal end that extends in a downwards direction away from slider 454 for locking or securing first coupler 451 and push rod 482 coupled thereto in an extended configuration as will be described in more detail herein. With additional reference to FIG. 10, second coupler 457 includes a lumen 459 there-through for receiving a proximal end 476 of intermediate shaft 474, as well as push rod 482 which is slidably disposed through intermediate shaft 474 and extends proximally to first coupler 451. A proximal portion of second coupler 457 also includes two spaced-apart rails 461A, 461B on opposing sides thereof for interaction or engagement with the pair of spaced-apart knobs or bosses 462A, 462B of slider 454. The proximal ends of rails 461A, 461B include grooves or notches 465A, 465B formed thereon for temporarily housing distal knobs 462A, 462B of slider 454 as will be described in more detail herein.

Figure 11A:
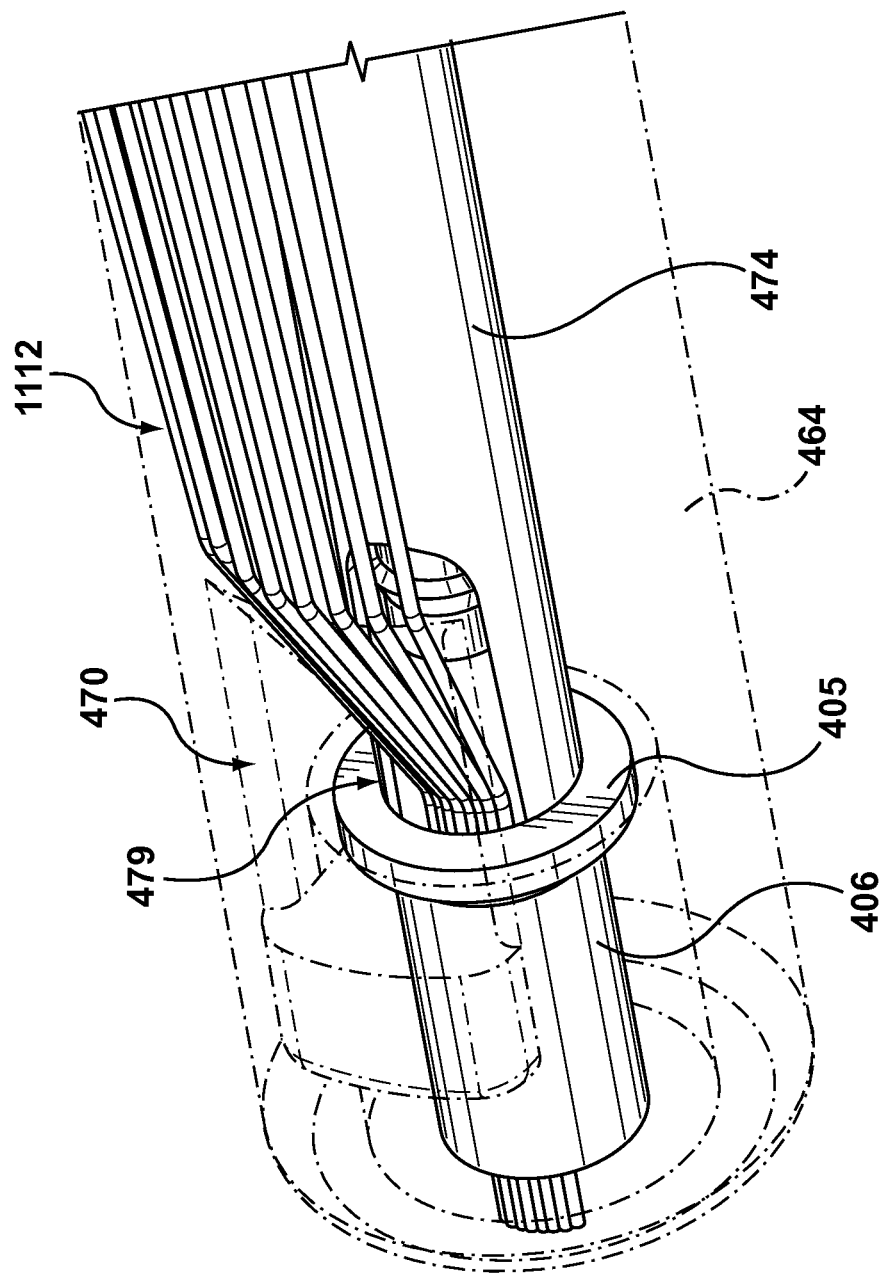
FIG. 11A is a perspective view of the distal end of the suture connector placement device of FIG. 4.
Figure 12A:
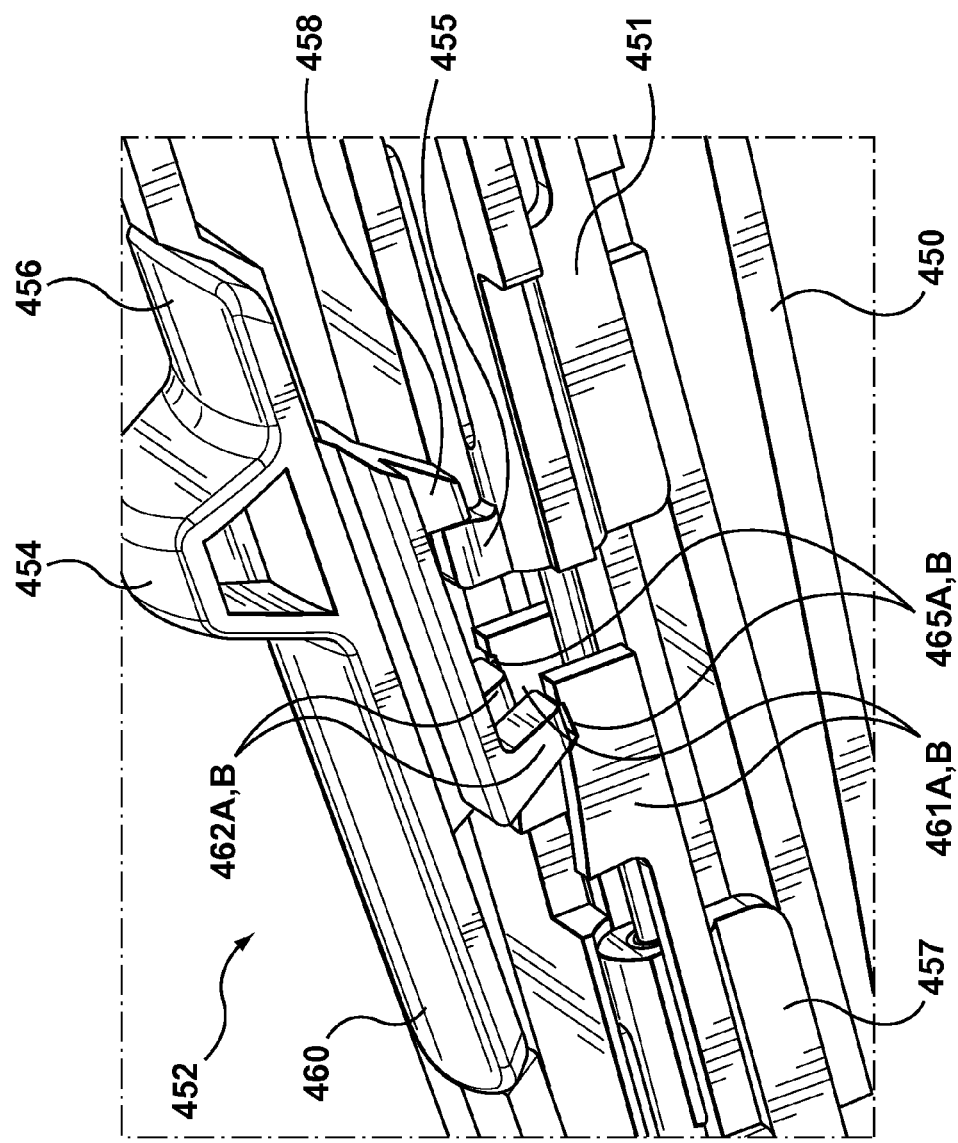
FIG. 12A is a perspective view of a portion of the handle of the suture connector placement device of FIG. 4.

Since suture connector placement device 402 is utilized to clamp or secure portions of one or more sutures within suture connector 404, the suture portions having been previously positioned around the border or edge of an arteriotomy of a vessel, the components of the suture connector placement device will be further described while simultaneously describing a method of using the suture connector placement device to secure two suture portions extending from an opening in body tissue with reference to FIGS. 11-20. Referring to FIGS. 11, 12, and 12A, side sectional views of suture connector placement device 402 are shown with a distal end of the suture connector placement device abutting against tissue having an arteriotomy $V_A$ in the vessel wall $V_W$ of a vessel. FIG. 11 is an enlarged view of only the distal end of the suture connector placement device while FIG. 12 illustrates handle 450 of the suture connector placement device as well. FIG. 11A is a perspective view of a distal end of the suture connector placement device and FIG. 12A is a perspective view of a portion of handle 450.

In FIGS. 11, 11A, 12, and 12A, suture connector 404 is in a loaded or delivery configuration within suture connector placement device 402. More particularly, when suture connector 404 is in the loaded configuration, sleeve 406 of suture connector 404 is radially disposed between outer shaft 464 and intermediate shaft 474 adjacent to distal end 468 of outer shaft 464. Stated another way, sleeve 406 of suture connector 404 is disposed on an outer surface of intermediate shaft 474 within lumen 472 of outer shaft 464 adjacent to distal end 468 of the outer shaft. Flange 405 of sleeve 406 abuts against or is adjacent to abutment surface 469 of outer shaft 464. Plug 408 of suture connector 404 is positioned within lumen 480 of intermediate shaft 474 proximal of the proximal end of sleeve 406. In addition, distal end 486 of push rod 482 is positioned proximal to a proximal end of plug 408. Distal end 478 of intermediate shaft 474 is positioned flush with the distal end of sleeve 406 as well as flush with distal end 468 of outer shaft 464. Side port 479 of intermediate shaft 474 is circumferentially aligned with side port 470 of outer shaft 464. Proximal end 456 of slider 454 abuts against a proximal surface 447 of recess 449 within handle 450, with knob 458 of slider 454 abutting against knob 455 of first coupler 451. Second coupler 457 is positioned within a distal portion of handle 450 such that the distal end of second coupler 457 abuts against an interior surface or stopper 441 formed within the distal portion of handle 450. As best shown in the perspective view of FIG. 12A, distal knobs 462A, 462B of slider 454 are positioned or housed within grooves or notches 465A, 465B formed on the proximal ends of rails 461A, 461B of second coupler 457.

Suture portions 1112 are shown positioned within the distal portion of suture connector placement device 402 in FIGS. 11-12. Suture portions 1112 enter into a distal end of the suture connector placement device, extend through lumen 407 of sleeve 406 of suture connector 404, and exit suture connector placement device 402 via aligned side ports 470, 479 of outer shaft 464, intermediate shaft 474, respectively. Suture portions 1112 are portions of one or more sutures that were previously positioned around the border or edge of arteriotomy $V_A$ in the vessel wall $V_W$ of a vessel. Exemplary suture materials include but are not limited to a monofilament or plastic suture material, such as polypropylene. In the loaded configuration of suture connector 404 of FIGS. 11-12, and as best shown in the perspective view of FIG. 11A, suture portions 1112 are positioned or extend into and through sleeve 406 via aligned side ports 470, 479 of outer shaft 464, intermediate shaft 474, respectively. In order to position or load the suture portions into the suture connector placement device, suture connector placement device 402 may include a preloaded threader (not shown) as described in U.S. Pat. Nos. 8,197,497 and 8,469,975 to Nobles et al., both of which were previously incorporated herein by reference. The threader includes a tab and a looped wire passing through side port 470 of outer shaft 464 and between sleeve 406 and intermediate shaft 474. Suture portions 1112 are passed through the looped end of the wire, and the tab is pulled proximally to dispose suture portions 1112 in the suture connector placement device through sleeve 406.

Suture portions 1112 may be held in tension, by hand or otherwise, while suture connector placement device 402 is advanced until distal end 468 contacts and abuts against an outer surface of the vessel wall around the border or edge of arteriotomy $V_A$. As shown in FIG. 11, distal end 468 of outer shaft 464 is sized to abut against the outer surface of the vessel wall $V_W$ and not protrude or extend through the arteriotomy $V_A$ and into the lumen L of the vessel. When the user is advancing suture connector placement device 402 to the arteriotomy $V_A$, a resistance to further advancement is felt when distal end 468 contacts the vessel wall, thereby notifying the user that the suture connector placement device is in place adjacent to the arteriotomy $V_A$ as desired.

When it is desired to begin deployment of suture connector 404, slider 454 is distally advanced in order to distally advance plug 408 towards sleeve 406 as shown in FIGS. 13 and 14. FIG. 13 is an enlarged view of only the distal end of the suture connector placement device while FIG. 14 illustrates handle 450 of the suture connector placement device as well. More particularly, when slider 454 of actuating mechanism 452 is distally advanced or pushed forward, knob 458 of slider 454 pushes or distally advances knob 455 of first coupler 451, thereby also distally advancing coupler 451 and push rod 482 attached thereto. Distal end 486 of push rod 482 contacts and distally advances plug 408 through intermediate shaft 474. Thus, distal advancement of slider 454 also distally advances push rod 482 and plug 408 in unison. During advancement of push rod 482, intermediate shaft 474 remains stationary with distal end 478 thereof positioned flush with distal end of sleeve 406 as well as flush with distal end 468 of outer shaft 464. Further, during distal advancement of push rod 482, distal knobs 462A, 462B of slider 454 exit or are removed from grooves or notches 465A, 465B formed on the proximal ends of rails 461A, 461B of second coupler 457, and distal knobs 462A, 462B ride along or over rails 461A, 461B of second coupler 457. More particularly, since the distal end of second coupler 457 abuts against stopper 441 formed within the distal portion of handle 450, second coupler 457 and intermediate shaft 474 coupled thereto are fixed or locked and cannot be inadvertently distally advanced during distal advancement of first coupler 451 and push rod 482. With second coupler 457 fixed, rails 461A, 461B are leaf springs and bend or flex in a downward direction away from slider 454 when distal knobs 462A, 462B of slider 454 are distally advanced there-over. In addition, sleeve 406 of suture connector 404 remains radially disposed between outer shaft 464 and intermediate shaft 474 adjacent to distal end 468 of outer shaft 464 during advancement of push rod 482. Suture portions 1112 may be held in tension, by hand or otherwise, during distal advancement of push rod 482 and plug 408.

Figure 16A:
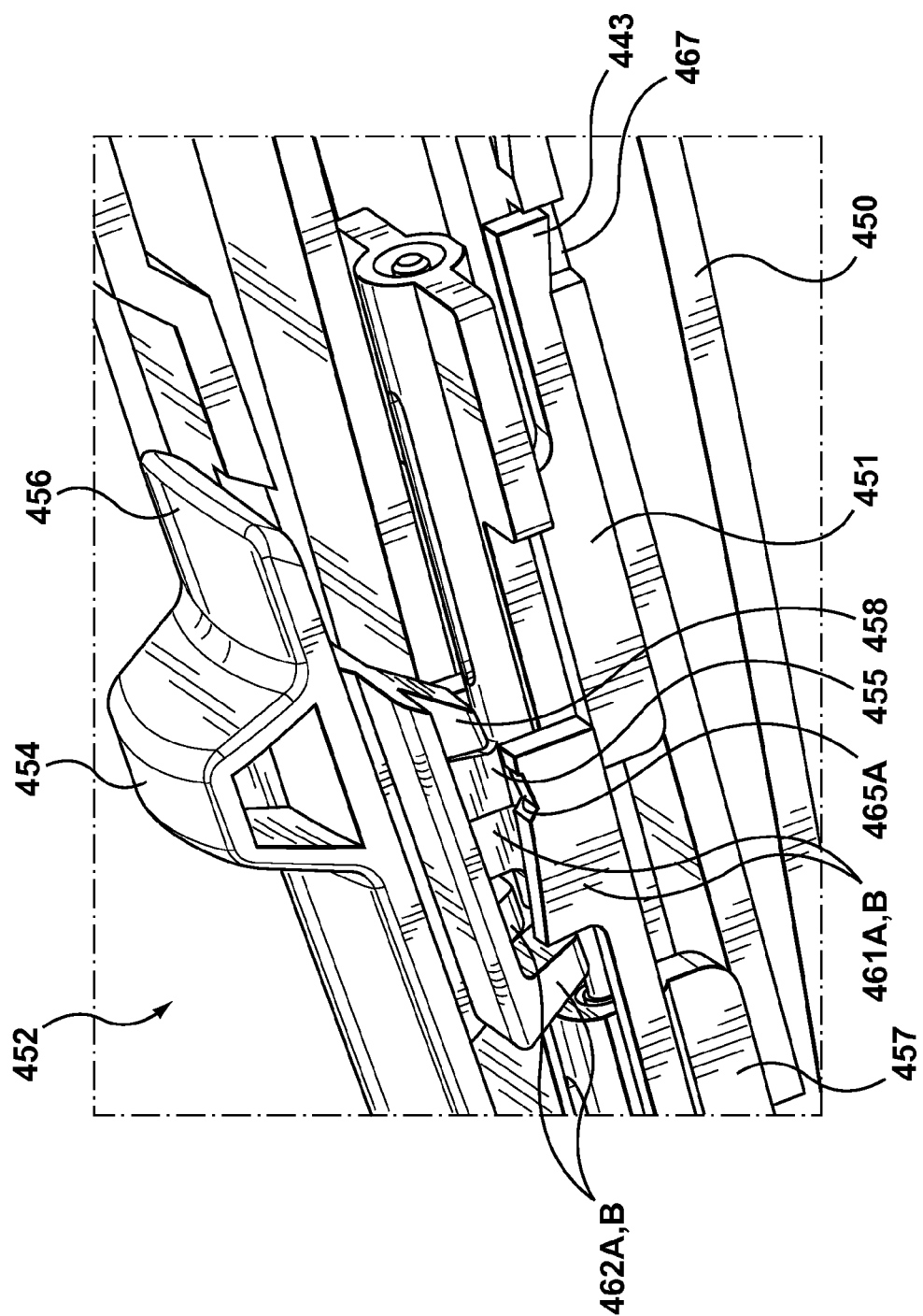
FIG. 16A is a perspective view of a portion of the handle of the suture connector placement device of FIG. 4.

Slider 454 is distally advanced to the position shown in FIGS. 15 and 16, in which distal end 460 thereof abuts against a distal surface 445 of recess 449 within handle 450 and plug 408 is positioned within sleeve 406. FIG. 15 is an enlarged view of only the distal end of the suture connector placement device while FIG. 16 illustrates handle 450 of the suture connector placement device as well. FIG. 16A is a perspective view of a portion of handle 450. Although plug 408 is positioned within sleeve 406, plug 408 and sleeve 406 are not yet in contact with each other because intermediate shaft 474 is radially positioned there-between. At this point in the method of use, slider 454 and push rod 482 are each in an extended position and suture connector 404 may be considered to be in a pre-deployed configuration since plug 408 of suture connector 404 has been extended or relocated into sleeve 406 but is not yet in contact with sleeve 406. As best shown in FIG. 16A, when slider 454 and push rod 482 are in the extended configuration, dovetail 443 at the proximal end of first coupler 451 extends into or is housed within a recess or notch 467 formed within handle 450 for locking or securing first coupler 451 and push rod 482 coupled thereto in the extended configuration. With slider 454 in the extended position, distal knobs 462A, 462B of slider 454 pass over or are now located distal to rails 461A, 461B of second coupler 457. After distal knobs 462A, 462B of slider 454 are no longer causing rails 461A, 461B to bend or flex downward due to their leaf spring characteristics, rails 461A, 461B spring upward and assume their nominal positions, with distal knobs 462A, 462B engaging or abutting against distal surfaces 463A, 463B of rails 461A, 461B. Advantageously, suture portions 1112 may still be adjusted or tightened at this stage of deployment. Thus, if distal advancement of plug 408 causes loosening or movement of suture portions 1112, tension or other adjustments may be applied to suture portions 1112 during or after the step of positioning of plug 408 within sleeve 406.

Figure 10:
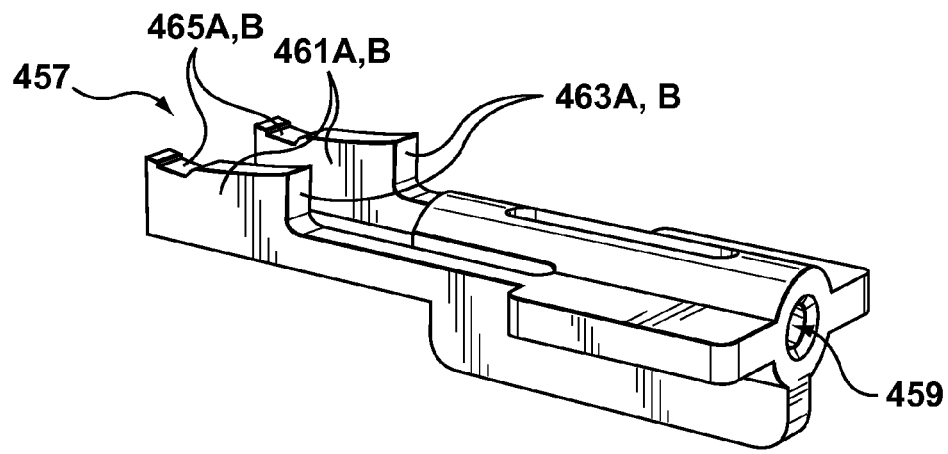
FIG. 10 is a perspective view of a second coupler of an actuating mechanism of the system of FIG. 6, wherein the second coupler is removed from a handle of the system for sake of illustration only.
Figure 17:
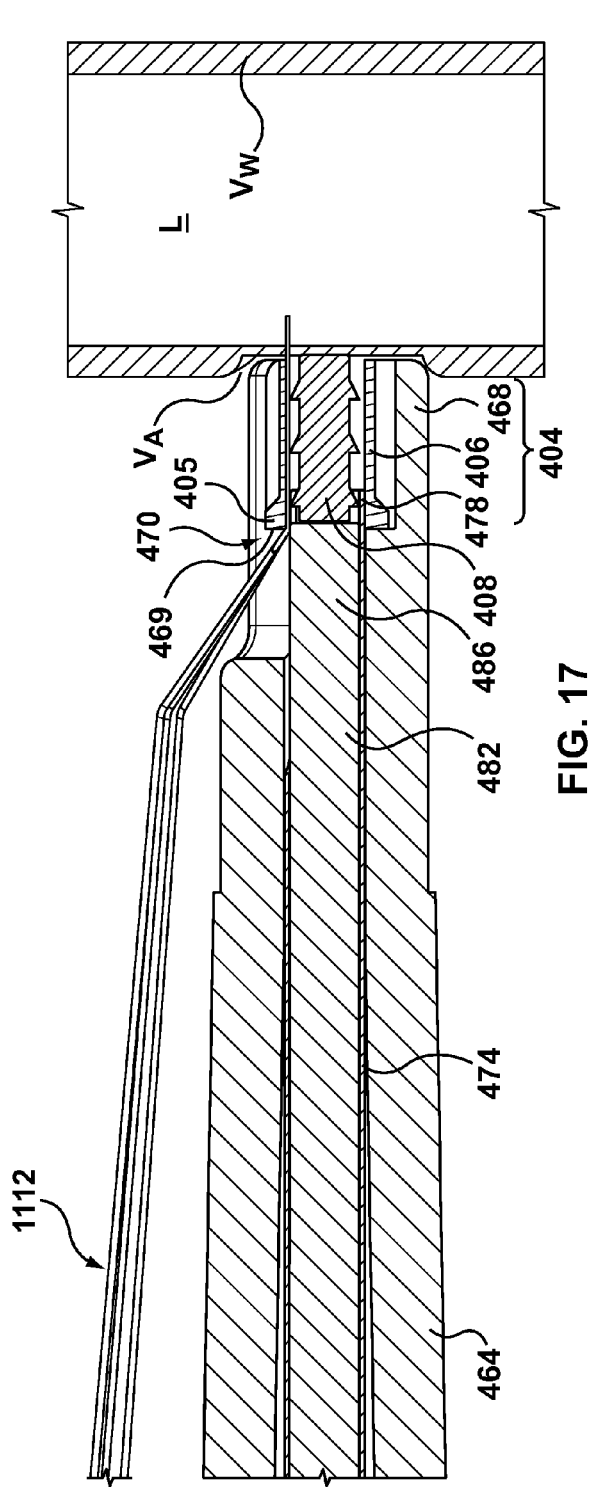
FIG. 17 is an enlarged side sectional view of a distal end of the suture connector placement device of FIG. 4 abutting against tissue having an arteriotomy $V_A$ in the vessel wall $V_W$ of a vessel, wherein the intermediate shaft of the suture connector placement device is shown being retracted.
Figure 18:
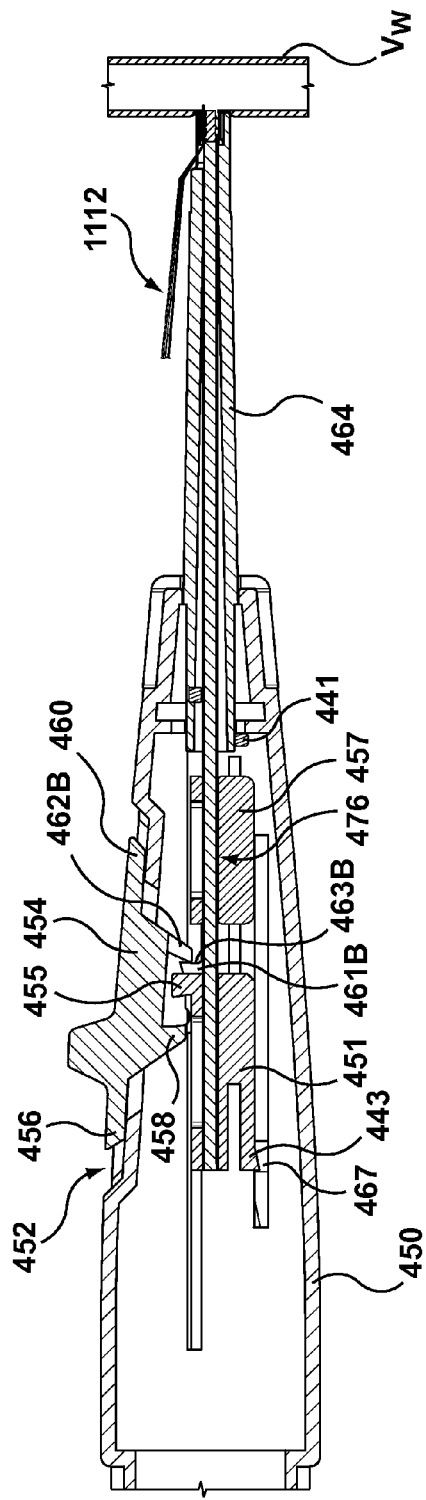
FIG. 18 is a side sectional view of the suture connector placement device of FIG. 4 abutting against tissue having an arteriotomy $V_A$ in the vessel wall $V_W$ of a vessel, wherein the intermediate shaft of the suture connector placement device is shown being retracted.

Once suture portions 1112 have been adjusted or tightened as desired, intermediate shaft 474 is proximally retracted in order to release sleeve 406 onto plug 408. More particularly, when it is desired to complete deployment of suture connector 404, slider 454 is proximally retracted in order to proximally retract intermediate shaft 474 away from sleeve 406 as shown in FIGS. 17 and 18. FIG. 17 is an enlarged view of only the distal end of the suture connector placement device while FIG. 18 illustrates handle 450 of the suture connector placement device as well. More particularly, when slider 454 of actuating mechanism 452 is proximally retracted or pulled backwards, the pair of knobs 462A, 462B of slider 454 engages or abuts against distal surfaces 463A, 463B of rails 461A, 461B of second coupler 457. Although FIG. 15 is a sectional view and only knob 462B and rail 461B are shown, knob 462A and rail 461A are mirror images of knob 462B and rail 461B, respectively, as shown in FIG. 10, and as such, interactions there-between are the same. Slider 454 thus pushes or proximally retracts rails 461A, 461B of second coupler 457, thereby also proximally retracting second coupler 457 and intermediate shaft 474 attached thereto. During retraction of intermediate shaft 474 knob 458 of slider 454 is no longer in contact with knob 455 of first coupler 451 and passes or slides within a space between rails 461A, 461B of second coupler 457, such that push rod 482 remains stationary in the extended position during retraction of intermediate shaft 474. In addition, dovetail 443 at the proximal end of first coupler 451 being locked or secured within recess or notch 467 of handle 450 ensures that push rod 482 (which is attached to first coupler 451) is not inadvertently retracted with intermediate shaft 474. With push rod 482 locked in the extended position, plug 408 remains securely within sleeve 406 during retraction of intermediate shaft 474. In addition, during retraction of intermediate shaft 474, flange 405 formed on sleeve 406 engages or abuts against abutment surface 469 formed within outer shaft 464 to ensure that sleeve 406 is not inadvertently retracted with intermediate shaft 474. Thus, the interaction between abutment surface 469 and flange 405 of sleeve 406 ensures that sleeve 406 is held stationary when intermediate shaft 474 is retracted.

Figure 20A:
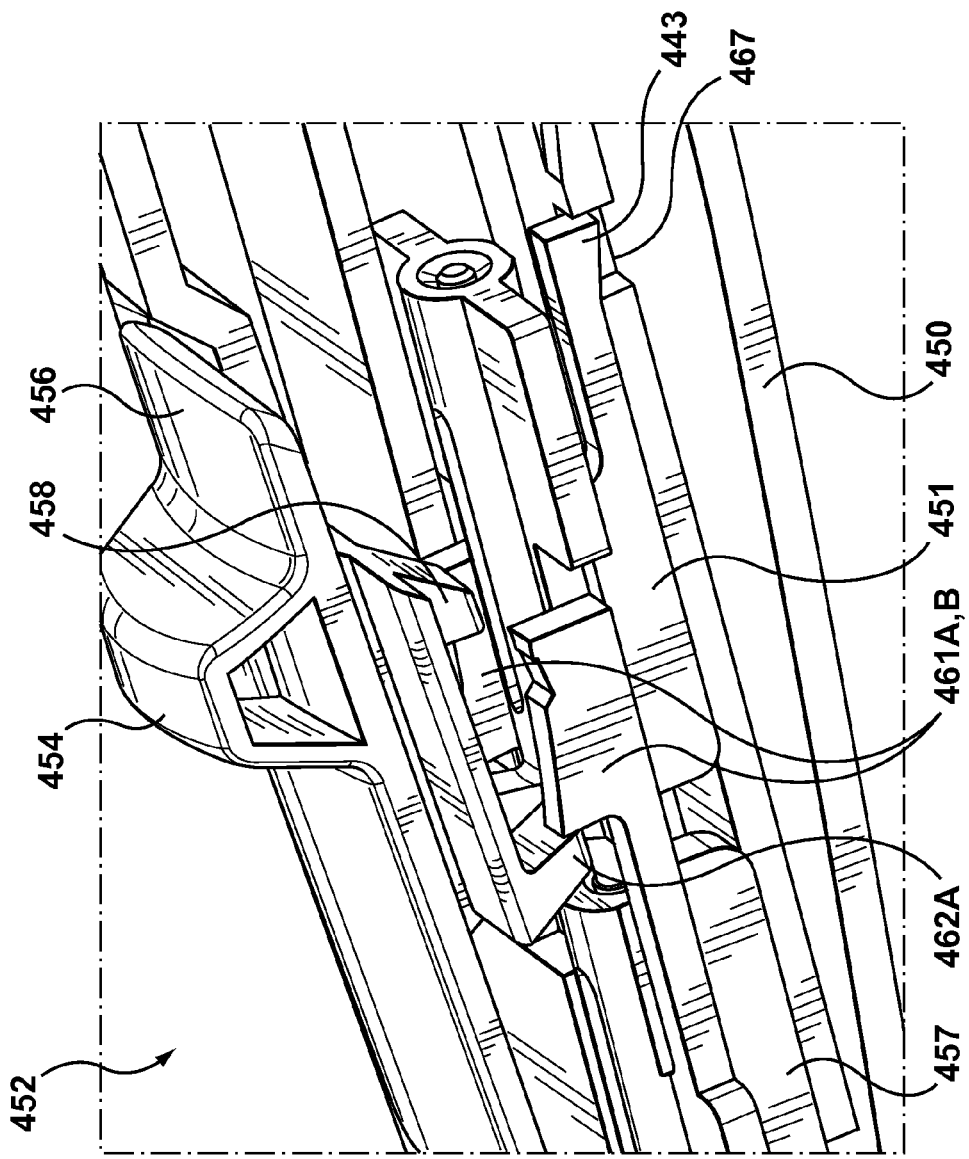
FIG. 20A is a perspective view of a portion of the handle of the suture connector placement device of FIG. 4.

Slider 454 is proximally retracted to the position shown in FIGS. 19 and 20, in which proximal end 456 thereof abuts against proximal surface 447 of recess 449 within handle 450 and distal end 478 of intermediate shaft 474 is positioned proximal to proximal ends of plug 408 and sleeve 406. FIG. 19 is an enlarged view of only the distal end of the suture connector placement device while FIG. 20 illustrates handle 450 of the suture connector placement device as well. FIG. 20A is a perspective view of a portion of handle 450. With intermediate shaft 474 removed from between plug 408 and sleeve 406, sleeve 406 is released to contact or clamp onto plug 408 thereby securing suture portions 1112 between the sleeve and the plug. Stated another way, when intermediate shaft 474 is retracted, sleeve 406 is no longer in contact with the outer surface of intermediate sleeve 474 and sleeve 406 thereby releases onto plug 408, thereby enveloping, covering, wrapping around or otherwise surrounding plug 408. When sleeve 406 is released onto plug 408, radial protrusions 409 of plug 408 may compress or flatten due to the contact between the sleeve and the plug, thereby ensuring an interference or press fit there-between. In an embodiment hereof, sleeve 406 is formed from a resilient or elastic material such as but not limited to an elastomer. In an embodiment hereof, sleeve 406 is formed from silicone. In the loaded configuration of suture connector 404 discussed above, sleeve 406 is stretched or expanded over intermediate shaft 474 and when intermediate shaft 474 is retracted, sleeve 406 resiliently contracts or compresses onto plug 408. At this point in the method of use, slider 454 and intermediate shaft 474 are each in a retracted position and suture connector 404 is in a fully deployed configuration since plug 408 is in contact with sleeve 406 with suture portions 1112 sandwiched there-between. Stated another way, when sleeve 406 is released onto plug 408, suture portions 1112 extending between the plug and the sleeve are thereby secured or fixed relative to each other within the formed suture connector 404.

In another embodiment hereof, in order to ensure contact between plug 408 and sleeve 406 of suture connector 404 upon retraction of intermediate shaft 474, the plug of the suture connector may be formed from a resilient or elastic material in addition to or as an alternative to forming the sleeve of a resilient material. More particularly, plug 408 may be formed from a resilient material that is slightly compressed into intermediate shaft 474 such that plug 408 is still moveable relative to or slideable within the intermediate shaft. After plug 408 has been longitudinally positioned within sleeve 406 and intermediate shaft 474 is retracted, plug 408 may resiliently radially expand into contact with sleeve 406 thereby securing suture portions 1112 between the sleeve and the plug.

Upon retraction of intermediate shaft 474, suture connector 404 is still disposed within the outer shaft of the suture connector placement device 402 but has been decoupled therefrom such that the suture connector remains in situ when the suture connector placement device is proximally retracted. Accordingly, when suture connector placement device 402 is proximally retracted and removed from the patient, suture connector 404 remains in situ with suture portions 1112 secured therein. Since it is not required to push or eject suture connector 404 from suture connector placement device 402, suture connector 404 may be formed from less rigid or less stiff materials than would otherwise be required if suture connector 404 had to be pushed or ejected from suture connector placement device 402. In an embodiment hereof, sleeve 406 is formed from silicone and plug 408 is formed from collagen. Such materials are very biocompatible and may be preferred over rigid or stiff materials that would otherwise be required if suture connector 404 was to be pushed or ejected from suture connector placement device 402. In another embodiment hereof, sleeve 406 and plug 408 may be formed from more rigid biocompatible materials such as but not limited to polypropylene.

In addition to the material of suture connector 404, other advantages flow or result from the fact sleeve 406 is resiliently released onto plug 408 via retraction of the intermediate shaft and there is no requirement to push or eject the formed connector out of the device. More particularly, pushing or ejecting the formed connector out of the suture connector placement device may result in pushing the suture connector through arteriotomy $V_A$ in the vessel wall $V_W$ of a vessel. If inadvertently pushed through the arteriotomy, suture connector 404 may contact and damage the inner vessel wall opposite the incision/arteriotomy. Further, if inadvertently pushed through the arteriotomy, suture connector 404 may not result in full closure and hemostasis at the treatment site.

FIGS. 21, 22, and 23 illustrate another embodiment of a suture connector placement device 2101. Suture connector placement device 2101 includes a handle 2150 and outer shaft 2164 and is similar to connector placement 402 described above, except that suture connector placement device 2101 further includes an outermost shaft 2188 rotatably disposed over outer shaft 2164. Outermost shaft 2188 is a tubular component having a proximal end 2190 disposed adjacent to handle 2150 and a distal end 2192 disposed proximal to side port or opening 2170 of outer shaft 2164. Outermost shaft 2188 defines a lumen 2194 (shown in phantom in FIG. 21) there-through. Distal end 2192 of outermost shaft 2188 includes a cutting surface 2196 that is operable to sever a suture. The proximal end 2190 of outermost shaft 2188 includes a wheel 2198 for rotating the outer shaft relative to outer shaft 2164. After a suture connector is formed, i.e., after a plug is in contact with a sleeve with suture portions sandwiched there-between, a user may rotate outermost shaft 2188 relative to outer shaft 2164 via wheel 2198 and cutting surface 2196 severs the suture portions adjacent to where they extend out of side port 2170 of outer shaft 2164. In another embodiment, the suture portions may be cut manually.

FIG. 24 illustrates a side view of a suture connector placement device 2402 configured for positioning a knot or suture connector 2404 in situ according to another embodiment hereof. Suture connector 2404 may be used to secure suture portions that are positioned adjacent to an opening or arteriotomy of a blood vessel or other biological tissue following an interventional catheterization procedure, thereby closing or sealing the opening or arteriotomy to achieve hemostasis. FIG. 25 is a side view of suture connector 2404. Collectively, suture connector placement device 2402 and suture connector 2404 may be considered a system 2400 for forming a suture connector in situ. Suture connector placement device 2402 includes a handle 2450 having an actuating mechanism 2452 therein and an outer shaft 2464 distally extending from handle 2450. Suture connector 2404 includes a cylindrical component or plug 2408 and a tubular component or sleeve 2406 which defines a lumen 2407 there-through. Plug 2408 has an outer dimension and a length configured to be inserted into the lumen 2407 of sleeve 2406. Plug 2408 may include radial protrusions 2409 extending from its outer surface to ensure an interference or press fit between plug 2408 and sleeve 2406 when the plug and the sleeve are assembled or joined as will be described in more detail herein. Protrusions 2409 may be rings, spirals, spikes, bumps, or other suitable structures. When loaded into suture connector placement device 2402, as will be explained in more detail below, sleeve 2406 extends from a distal end of outer shaft 2464 and plug 2408 is disposed within a distal end of outer shaft 2464 such that plug 2408 is positioned proximal of sleeve 2406.

However, unlike suture connect placement device 402, in this embodiment an intermediate shaft 2474 of suture connector placement device 2402 is slidingly and rotatably disposed within the lumen of outer shaft 2464. More particularly, intermediate shaft 2474 is permitted to slide or move axially relative to outer shaft 2464 during certain stages or steps of operation and then is permitted to rotate relative to outer shaft 2464 during other stages or steps of deployment. Stated another way, intermediate shaft 2474 is configured to be slidingly disposed within the lumen of outer shaft 2464 in a first configuration and is configured to be rotatably disposed within the lumen of outer shaft 2464 in a second configuration but is not configured to slide and rotate at the same time. Operation of suture connector placement device 2402 to fully deploy and form suture connector 2404 in situ and trim the sutures from the formed suture connector 2404 may be considered a three-stage or three-step process. In a first step or stage of operation of suture connector placement device 2402 that will be described in more detail herein, suture connector placement device 2402 causes plug 2408 to be distally advanced or pushed into sleeve 2406, although sleeve 2406 and plug 2408 are not yet in contact with each other at this stage of operation. Intermediate shaft 2474 is fixed during this first stage of operation. Once the sleeve and plug are longitudinally aligned with each other, with both extending from a distal end of outer shaft 2464, suture connector 2404 is in a pre-deployed configuration. In a second step or stage of operation of suture connector placement device 2402 that will be described in more detail herein, suture connector placement device 2402 causes sleeve 2406 to be released onto plug 2408, thereby securing or clamping suture portions (not shown in FIGS. 24-25) between the plug and the sleeve to thereby secure or hold the suture portions together relative to each other within the formed connector. The suture portions are secured or coupled together via the interference or press fit between plug 2408 and sleeve 2406. Once the sleeve is released onto the plug, suture connector 2404 is formed and in a fully deployed configuration. Intermediate shaft 2474 is permitted or configured to slide or move axially during this second stage of operation. In a third step or stage of operation of suture connector placement device 2402 that will be described in more detail herein, suture connector placement device 2402 trims the suture portions. Intermediate shaft 2474 is permitted or configured to rotate during this third stage of operation.

Similar to suture connector placement device 402, suture connector placement device 2402 includes outer shaft 2464, intermediate shaft 2474, a push rod 2482, and handle 2450 having actuating mechanism 2452 which includes a slider 2454, a first coupler 2451, and a second coupler 2457. These components of suture connector placement device 2402 may be made of any suitable material, including but not limited to metals, plastics, and a combination of metals and plastics. Intermediate shaft 2474 is slidingly or rotatably disposed through a lumen 2472 of outer shaft 2464 (depending upon the stage of operation), and push rod 2482 is slidingly disposed through a lumen 2480 of intermediate shaft 2474. Outer shaft 2464 is an elongate tubular component defining lumen 2472 and has a proximal end 2466 (shown on FIG. 29) that extends into and is coupled to handle 2450. Outer shaft 2464 also includes a side opening or port 2470 proximal to its distal end 2468.

Figure 26:
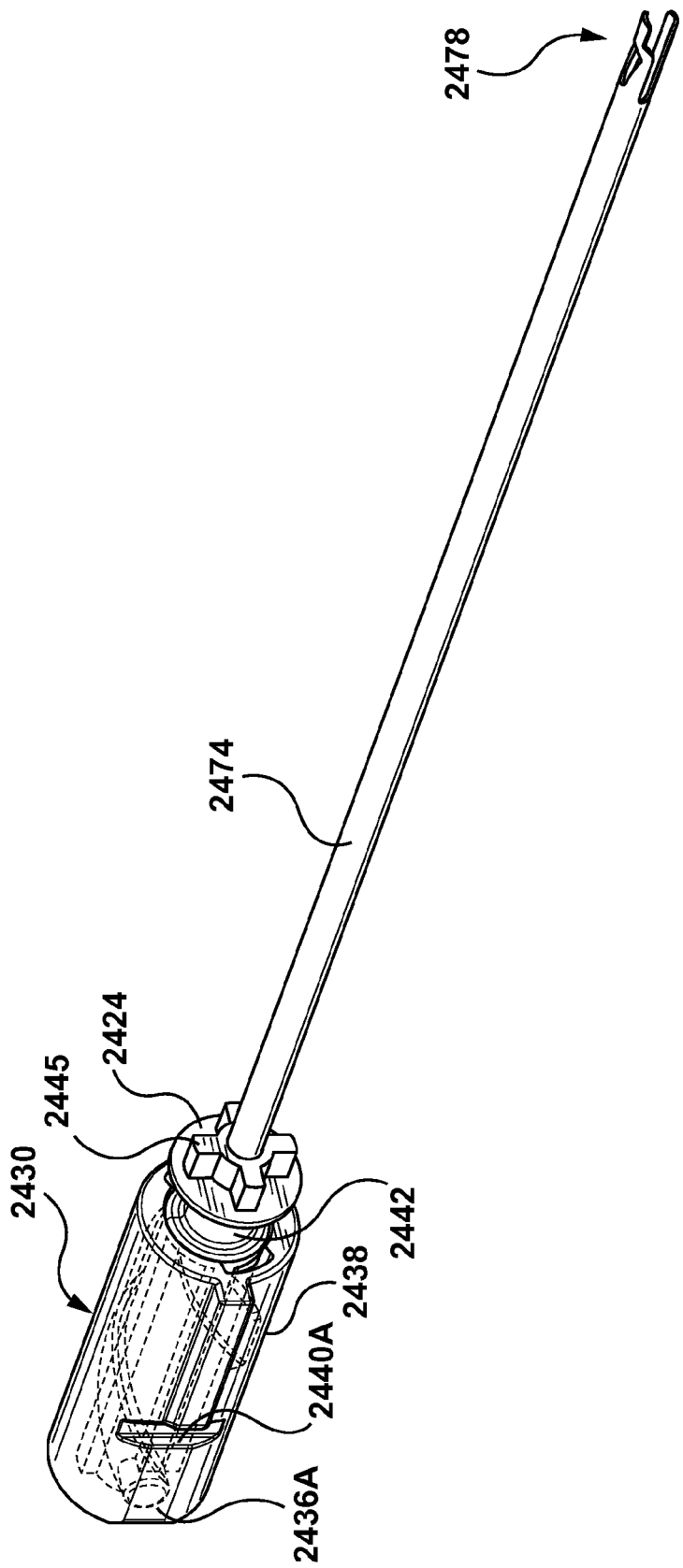
FIG. 26 is a perspective view of the intermediate shaft of the suture connector placement device of FIG. 24, wherein the intermediate shaft is removed from the suture connector placement device for illustrative purposes only.
Figure 26A:
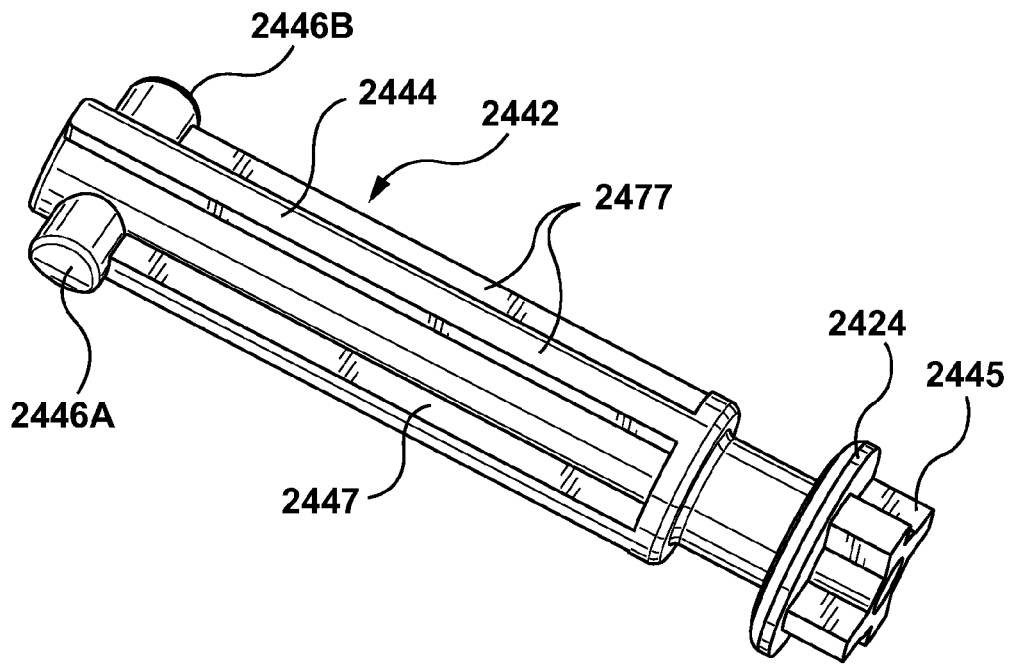
FIG. 26A is a perspective view of a tubular overmold portion formed over a proximal end of the intermediate shaft of FIG. 26, wherein the tubular overmold portion is removed from the suture connector placement device for illustrative purposes only.
Figure 26B:
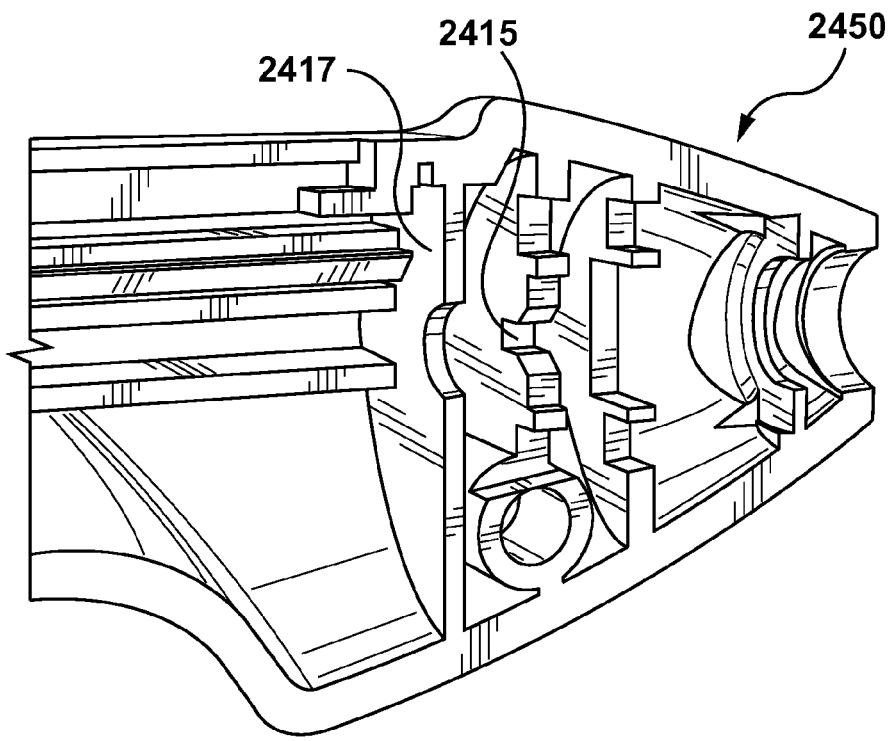
FIG. 26B is a side view of a proximal portion of a handle of the suture connector placement device of FIG. 24.
Figure 28:
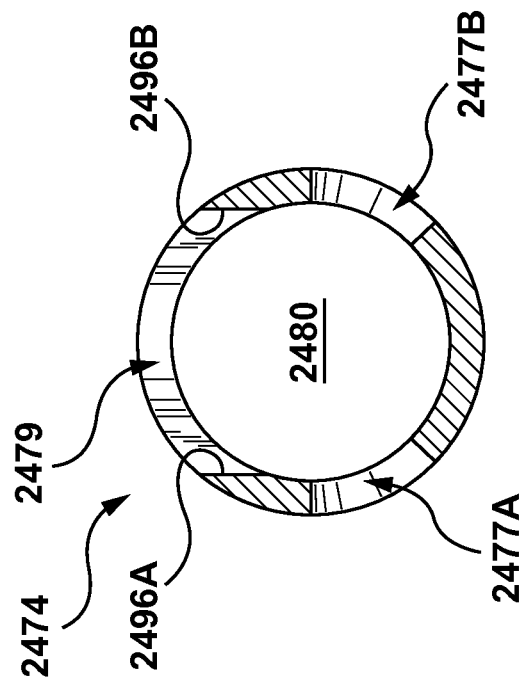
FIG. 28 is a sectional view of the distal end of the intermediate shaft of FIG. 26.
Figure 27:
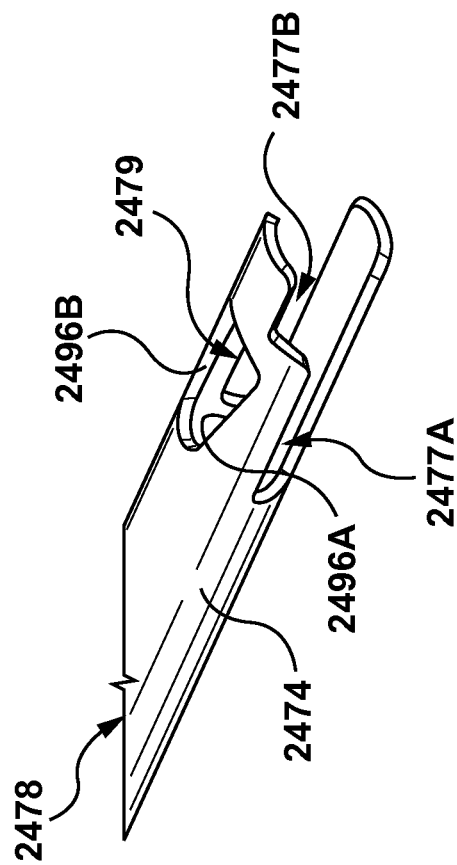
FIG. 27 is an enlarged view of a distal end of the intermediate shaft of FIG. 26.

Intermediate shaft 2474 will now be described in more detail with reference to FIG. 26, which is a perspective view of intermediate shaft 2474 removed from suture connector placement device 2402 for illustrative purposes only. FIG. 27 is an enlarged view of the distal end portion of FIG. 26, and FIG. 28 is a sectional view of the distal end portion of FIG. 26. Intermediate shaft 2474 is a tubular component defining lumen 2480. FIG. 26B is a side view of a proximal portion of handle 2450. As best shown on FIG. 26A, intermediate shaft 2474 includes a tubular overmold portion 2442 formed over the proximal end thereof that includes two opposing pegs or bosses 2446A, 2446B which each radially extend from an outer surface 2444 thereof. FIG. 26A is a perspective view of tubular overmold portion 2442 removed from the suture connector placement device for illustrative purposes only. Tubular overmold portion 2442 also includes four longitudinally-extending ribs 2447 (only three of which are shown in the perspective view of FIG. 26A) which each radially extend from an outer surface 2444 thereof and are equally spaced around the circumference thereof. The proximal end of intermediate shaft 2474, including tubular overmold portion 2442, extends into a lumen 2432 of a tubular component herein referred to as a lead 2430. Pegs 2446A, 2446B of tubular overmold portion 2442 interface with lead 2430 as will be described in more detail herein, and longitudinally-extending ribs 2447 function to maintain concentricity of the tubular overmold portion (and intermediate shaft 2470 attached thereto) during operation. Overmold portion 2442 includes a flange 2424 formed at a distal end thereof, distal to lead 2430. On its distal surface, flange 2424 includes a distally-extending crosshair extension 2445 that interfaces with crosshair grooves 2415 of handle 2450 (shown on handle view of FIG. 26B) to prevent rotational movement of intermediate shaft 2474 relative to outer shaft 2464 and push rod 2482 during certain stages of deployment. Crosshair grooves 2415 include a total of four recesses or grooves within handle 2450 that collectively form a cross or plus-sign shape, although FIG. 26B shows only a single groove thereof. As will be understood by one of ordinary skill in the art, although crosshair grooves 2415 include four recesses or grooves configured to mate with distally-extending crosshair extension 2445 of flange 2424, the shape of the extension (and the mating shape and number of grooves or recesses formed within the handle) may vary and have numerous other patterns or configurations. As will be explained in more detail herein with reference to FIGS. 44 and 45, lead 2430 is coupled to the proximal end of intermediate shaft 2474 to permit rotational movement of intermediate shaft 2474 relative to outer shaft 2464 and push rod 2482 during certain stages of deployment. Perspective and side views, respectively, of lead 2430 are shown in FIGS. 44 and 45, respectively. An outer surface 2438 of lead 2430 includes opposing flattened or truncated surfaces 2436A, 2436B on a proximal end thereof for interacting with second coupler 2457 of actuating mechanism 2452 as will be described in more detail herein with respect to FIG. 32. Flattened surfaces 2436A, 2436B may alternatively be grooves or channels (not shown) formed on outer surface 2438 of lead 2430. Outer surface 2438 also includes opposing notches or recesses 2440A, 2440B at a distal end of each flattened surface 2436A, 2436B, which are configured to couple second coupler 2457 to lead 2430 as will be described in detail herein with respect to FIG. 32.

When assembled into suture connector placement device 2402, a distal end 2478 of intermediate shaft 2474 extends beyond or distal to distal end 2468 of outer shaft 2464 and is configured to receive sleeve 2406 thereover. Intermediate shaft 2474 also includes side window or port 2479 proximal to its distal end 2478 and a plurality of opposing side slots or openings 2477A, 2477B. Side window 2479 includes opposing cutting surfaces 2496A, 2496B. When intermediate shaft 2474 is rotated, suture portions (not shown on FIG. 28) that extend through side window 2479 are trimmed via one of cutting surfaces 2496A, 2496B as will be explained in more detail herein with respect to FIG. 43. In an embodiment, intermediate shaft 2474 is formed from a hypotube of stock 304 Stainless Steel. All faces of opposing side slots 2477A, 2477B are laser cut perpendicular to the hypotube wall, while all faces of side window 2479 (including cutting surfaces 2496A, 2496B) are milled out in a single axis cut which inherently sharpens the outer wall as the cut nears the side wall of the hypotube. By single-axis milling all faces of side window 2479, the further the cut extends away from the center axis, the sharper the edge will be. Accordingly, the faces of side window 2479 form a spectrum of acute edges, with the exception of the center line which will be 90 degrees. Cutting surfaces 2496A, 2496B are formed by the faces of side window 2479 that are sufficiently sharp to cut or trim the suture portions. Prior to rotation of intermediate shaft 2474, i.e., when side ports 2470 of outer shaft 2464, intermediate shaft 2474, respectively, are circumferentially aligned, cutting surfaces 2496A, 2496B are hidden within or covered by outer shaft 2464.

Side slots 2477A, 2477B of intermediate shaft 2474 are of a pre-formed width and extend to distal end 2478 of intermediate shaft 2474, or stated another way, extend in a proximal direction from distal end 2478 of intermediate shaft 2474. As will be described in more detail herein with respect to the loaded configuration of suture connector placement device 2402, side slots 2477A, 2477B permit distal end 2478 of intermediate shaft 2474 to flex and compress when sleeve 2406 is positioned thereover, thus reducing strain on the sleeve when suture connector placement device 2402 is stored in its loaded or delivery configuration. When plug 2408 is pushed into position within lumen 2407 of sleeve 2406, intermediate shaft 2474 opens to its original or pre-formed diameter to guide the plug inside the sleeve during deployment and side slots 2477A, 2477B resume to their pre-formed width.

Figure 29:
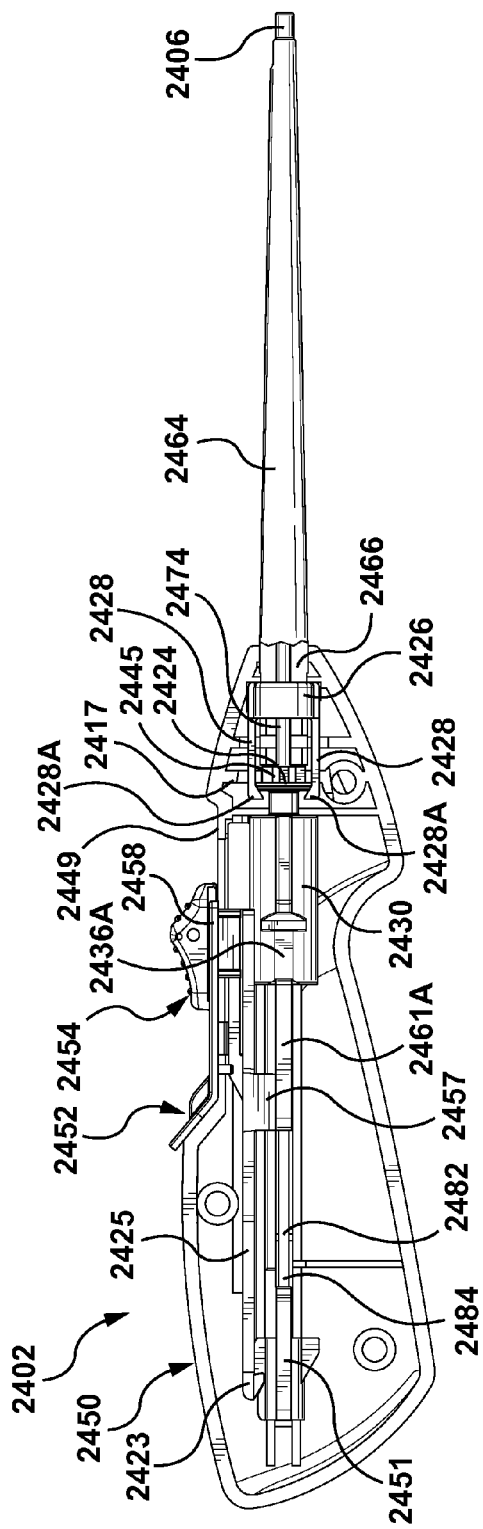
FIG. 29 is a sectional view of the suture connector placement device of FIG. 24, wherein the suture connector is in a loaded or delivery configuration within the suture connector placement device.
Figure 31:
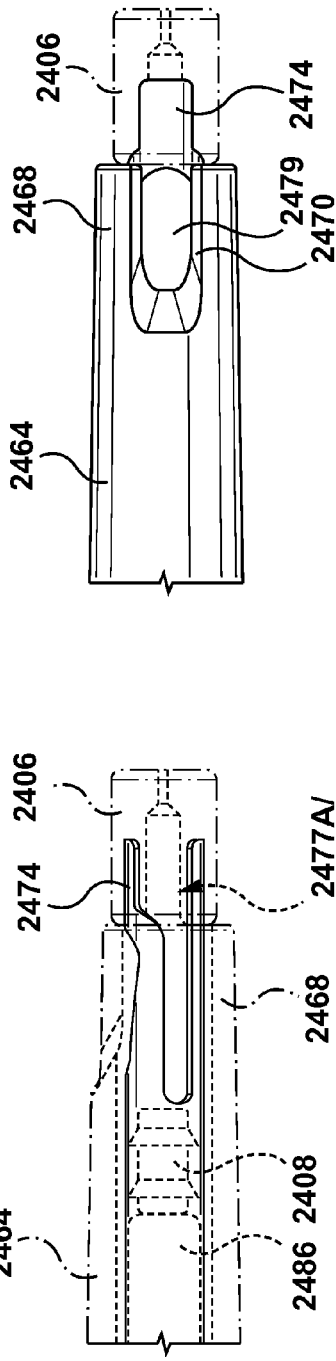
FIG. 31 is an enlarged side view of the distal end of FIG. 29.
Figure 30:
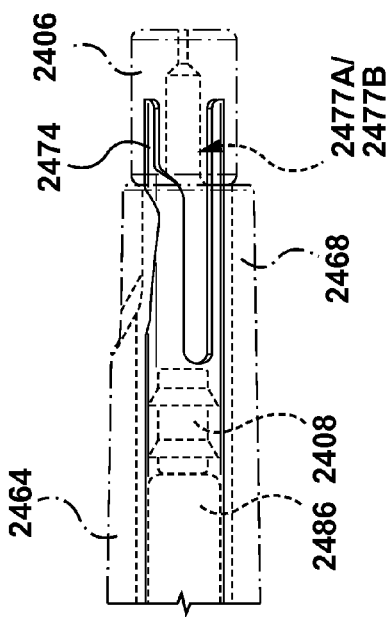
FIG. 30 is an enlarged side view of a distal end of FIG. 29.

Although sutures are not shown in FIGS. 29-45, suture connector placement device 2402 is utilized to clamp or secure portions of one or more sutures within suture connector 2404, the suture portions having been previously positioned around the border or edge of an arteriotomy of a vessel as described and shown with respect to suture connector placement device 402. As described above with respect to FIGS. 11-12, in order to position or load the suture portions into the suture connector placement device, suture connector placement device 2402 may include a preloaded threader (not shown) as described in U.S. Pat. Nos. 8,197,497 and 8,469,975 to Nobles et al., both of which were previously incorporated herein by reference. The threader includes a tab and a looped wire passing through side port 2470 of outer shaft 2464, through side window 2479 of intermediate shaft 2474, and through lumen 2407 of sleeve 2406. Suture portions are passed through the looped end of the wire, and the tab is pulled proximally to dispose the suture portions in the suture connector placement device through sleeve 2406 and through side window 2479 of intermediate shaft 2474. Suture portions enter into a distal end of the suture connector placement device, extend through lumen 2407 of sleeve 2406 of suture connector 2404, extend through side window 2479 of intermediate shaft 2470, and exit suture connector placement device 2402 via side port 2470 of outer shaft 2464. In the loaded configuration of suture connector 2404 of FIGS. 29-31, suture portions would be positioned or extend into and through sleeve 2406 via aligned side ports 2470, 2479 of outer shaft 2464, intermediate shaft 2474, respectively. FIG. 29 is a side sectional view of suture connector placement device 2402, and FIGS. 30 and 31 are enlarged side views of only the distal end of the suture connector placement device. Notably, as previously mentioned, when the suture portions positioned or loaded into the suture connector placement device, side ports 2470, 2479 of outer shaft 2464, intermediate shaft 2474, respectively, are circumferentially aligned and cutting surfaces 2496A, 2496B of side window 2479 are hidden within or covered by outer shaft 2464 so that the suture portions are protected or shielded from the cutting surfaces until the user desires to commit to cutting or trimming the sutures as will be explained in more detail herein.

In FIGS. 29-31, suture connector 2404 is in a loaded or delivery configuration within suture connector placement device 2402. More particularly, when suture connector 2404 is in the loaded configuration, sleeve 2406 of suture connector 2404 is disposed on an outer surface of intermediate shaft 2474 via an interference fit there-between. Stated another way, sleeve 2406 is disposed over distal end 2478 of intermediate shaft 2474. Unlike sleeve 406 which is disposed within lumen 472 of outer shaft 464, however, sleeve 2406 (and distal end 2478 of intermediate shaft 2474) extends beyond or from distal end 2468 of outer shaft 2464. Sleeve 2406 is disposed on an outer surface of intermediate shaft 2474 over opposing side slots 2477A, 2477B of distal end 2478, thereby compressing the opposing side slots and reducing their pre-formed widths as shown in the side view of FIG. 30. Sleeve 2406 may be formed from a Thermoplastic Polyether Urethane (TPU), a Thermoplastic Polycarbonate Polyurethane (PCU) such as Bionate™, or other elastomeric material. In an embodiment hereof, sleeve 2406 is injection molded of Elasthane 80A Thermoplastic Polyether Urethane (TPU) material which is biocompatible for a long term implant. In addition, Elasthane 80A Thermoplastic Polyether Urethane (TPU) has a high strength which is required to impart a strong normal force onto the suture portions after suture connector 2404 is deployed or formed, is aromatic which prevents hydrolysis, and is relatively flexible which allows sleeve 2406 to be stretched over intermediate shaft 2474 when suture connector placement device 2402 is stored in its loaded or delivery configuration.

Plug 2408 of suture connector 2404 is slidingly disposed within lumen 2480 of intermediate shaft 2474, proximal to sleeve 2406, when suture connector 2404 is in a loaded configuration within suture connector placement device 2402. Plug may be formed from a variety of biocompatible materials including but not limited to a Thermoplastic Polyether Urethane (TPU), Elasthane, a rigid polymeric material, or metal. In an embodiment hereof, plug 2408 is formed from Elasthane 75D Thermoplastic Polyurethane Elastomer, which is harder than the material of sleeve 2406 so that it will not deform after suture connector 2404 is deployed or formed. Plug 2408 may include a radiopaque additive to allow visualization of the formed suture connector 2404. In addition, distal end 2486 of push rod 2482 is positioned proximal to a proximal end of plug 2408. Side window 2479 of intermediate shaft 2474 is circumferentially aligned with side port 2470 of outer shaft 2464 as shown in the side view of FIG. 31.

In this embodiment, actuating mechanism 2452 includes slider 2454, first coupler 2451, and second coupler 2457. Actuating mechanism 2452 is configured to distally advance push rod 2482 via distal advancement of first coupler 2451, is configured to proximally retract intermediate shaft 2474 via proximal retraction of second coupler 2457, and is also configured to rotate intermediate shaft 2474 via continued or additional proximal retraction of second coupler 2457. Perspective views of first and second couplers 2451, 2457, are shown removed from suture connector placement device 2402 for illustrative purposes only in FIG. 32 and FIG. 33, respectively. Advantageously, from a user perspective, operation of actuating mechanism 2452 requires interaction with only slider 2454, with distal advancement of slider 2454 being employed in the first step or stage of operation to push plug 2408 into sleeve 2406, proximal retraction of slider 2454 being employed in the second step or stage of operation to retract intermediate shaft 2474 and thereby release sleeve 2406 onto plug 2408, and further or continued proximal retraction of slider 2454 being employed in the third step or stage of operation to rotate intermediate shaft 2474 and thereby trim the suture portions.

More particularly, slider 2454 is housed within a recess 2449 of the handle such that a top surface thereof is accessible to the user and a bottom or underside surface is coupled to a knob or boss 2458 of second coupler 2457 (shown in FIG. 32). Second coupler 2457 includes an elongated rail or extension 2425 having a knob or boss 2423 at a proximal end thereof for coupling to first coupler 2451. With additional reference to FIG. 33, first coupler 2451 includes a lumen (not shown in FIG. 33) through at least a portion thereof for receiving proximal end 2484 of push rod 2482. First coupler 2451 also includes a tab 2455 that extends in an upward direction towards slider 2454. Tab 2455 includes a notch or recess 2427 for interaction or engagement with knob or boss 2423 of second coupler 2457. First coupler 2451 also includes a dovetail 2443 that extends in a downwards direction away from slider 2454 for abutting against a portion of the handle during extension of first coupler 2451 and push rod 2482 coupled thereto as will be described in more detail herein. Dovetail 2443 at the proximal end of first coupler 2451 constrains or prevents first coupler 2451 from spinning within handle 2450, although first coupler 2451 is most likely not inclined to spin. A distal portion of first coupler 2451 also includes two spaced-apart wings 2419A, 2419B on opposing sides thereof. The distal ends of wings 2419A, 2419B include tabs or protrusions 2421A, 2421B that extend radially outward for engaging or coupling to opposing notches or recesses (not shown) formed on the inside of handle 2450 as will be described in more detail herein.

Referring back to FIG. 32, a distal portion of second coupler 2457 also includes two spaced-apart rails 2461A, 2461B on opposing sides thereof for interaction with pair of spaced-apart flattened surfaces 2436A, 2436B of lead 2430, which is attached to the proximal end of intermediate shaft 2474. The distal ends of rails 2461A, 2461B include tabs or protrusions 2465A, 2465B that extend radially inward for engaging or coupling to notches 2440A, 2440B of lead 2430 as will be described in more detail herein. With additional reference to FIG. 29, when suture connector placement device 2402 is in a loaded configuration, second coupler 2457 when disposed within handle 2450 extends between first coupler 2451 and lead 2430. Second coupler 2457 is coupled to first coupler 2451 due to knob or boss 2423 of second coupler 2457 being received or housed within notch or recess 2427 formed on first coupler 2451, as shown in FIG. 29. Rails 2461A, 2461B are positioned proximal to lead 2430, with tabs 2465A, 2465B being disposed adjacent to a proximal end of lead 2430. Slider 2454 is positioned approximately in the middle of recess 449 within handle 450, and second coupler 2457 is not yet coupled or engaged with lead 2430.

A proximal portion of handle 2450 includes a directional stopper 2426 disposed over intermediate shaft 2474. As will be explained in more detail herein, directional stopper 2426 permits proximal retraction of intermediate shaft 2474 and flange 2424 coupled thereto during the second stage of deployment, and also functions collectively with a stopper 2441 formed within a proximal portion of handle 2450 to restrict axial or longitudinal movement of intermediate shaft 2474 and flange 2424 coupled thereto during the third stage of operation. Directional stopper 2426 is an annular component that includes two opposing proximally-extending fingers 2428 that extend over flange 2424, which is coupled to the outer surface of intermediate shaft 2474 as described above. Proximal tips 2428A of proximally-extending fingers 2428 extend radially inward and are dimensioned such that the space or gap therebetween is smaller than an outer diameter of flange 2424.

Suture portions (not shown) that are disposed within the distal end of suture connector placement device 2402 may be held in tension, by hand or otherwise, while suture connector placement device 2402 is advanced until sleeve 2406 contacts and abuts against an outer surface of the vessel wall around the border or edge of arteriotomy $V_A$. When it is desired to begin deployment of suture connector 2404, slider 2454 and second coupler 2457 attached thereto via knob or boss 2458 is distally advanced in order to distally advance plug 2408 towards sleeve 2406 as shown in FIGS. 34-36. FIG. 34 is a side sectional view of suture connector placement device 2402, and FIGS. 35 and 36 are enlarged side views of only the distal end of the suture connector placement device.

More particularly, when slider 2454 and second coupler 2457 attached thereto are distally advanced or pushed forward, knob 2423 of second coupler 2457 pushes or distally advances tab 2455 of first coupler 2451, thereby also distally advancing first coupler 2451 and push rod 2482 attached thereto. Distal end 2486 of push rod 2482 contacts and distally advances plug 2408 through intermediate shaft 2474. Thus, distal advancement of slider 2454 also distally advances push rod 2482 and plug 2408 in unison. During advancement of push rod 2482, intermediate shaft 2474 remains stationary with distal end 2478 thereof positioned within sleeve 2406. More particularly, since flange 2424 of tubular overmold portion 2442 abuts against a stopper 2417 of handle 2450 (shown on FIG. 29; see also handle view of FIG. 26B) formed within a proximal portion of handle 2450, tubular overmold portion 2442 and intermediate shaft 2474 coupled thereto are fixed or locked and cannot be inadvertently distally advanced during distal advancement of second coupler 2457, first coupler 2451 and push rod 2482. Flange 2424 coupled to the outer surface of intermediate shaft 2474 as described above also remains stationary, and is positioned distal to proximal tips 2428A of proximally-extending fingers 2428 of directional stopper 2426. Distal advancement of push rod 2482 moves plug 2408 to longitudinally position the plug within sleeve 2406, thereby expanding opposing side slots 2477A, 2477B of intermediate shaft 2474 to return to their pre-formed widths.

Further, during distal advancement of push rod 2482, rails 2461A, 2461B of second coupler 2457 ride along or over flattened surfaces 2436A, 2436B of lead 2430, which is attached to the proximal end of intermediate shaft 2474. Lead 2430 remains stationary during advancement of push rod 2482 because pegs 2446A, 2446B of tubular overmold portion 2442 interface with two opposing spiral pathways or threads 2435 formed on an inner surface of the lead as will be described in more detail with respect to FIG. 45. Since pegs 2446A, 2446B of tubular overmold portion 2442 extend into and are housed within lead 2430, the lead is held in place and constrained from distal movement. With lead 2430 fixed, rails 2461A, 2461B are leaf springs and bend or flex in a radially outward direction away from lead 2430 when rails 2461A, 2461B are distally advanced there-over. In addition, sleeve 2406 of suture connector 2404 remains disposed over intermediate shaft 2474 and extending from distal end 2468 of outer shaft 2464 during advancement of push rod 2482. Slider 2454 is distally advanced until a distal end thereof abuts against a distal end of recess 2449 and plug 408 is positioned within sleeve 406. After being advanced over flattened surfaces 2436A, 2436B of lead 2430, rails 461A, 461B spring radially inward and assume their nominal positions, with tabs or protrusions 2465A, 2465B at the distal ends of rails 2461A, 2461B of second coupler 2457 engaging or extending into notches 2440A, 2440B of lead 2430 to thereby couple second coupler 2457 and lead 2430 together.

At this point in the method of use, slider 2454 and push rod 2482 are each in an extended position and suture connector 2404 may be considered to be in a pre-deployed configuration since plug 2408 of suture connector 2404 has been extended or relocated into sleeve 2406 but is not yet in contact with sleeve 2406. As best shown in FIG. 34, when slider 2454 and push rod 2482 are in the extended configuration, dovetail 2443 at the proximal end of first coupler 2451 abuts against a stopper 2467 formed within handle 2450 for preventing further or additional distal advancement the first coupler and push rod coupled thereto. In addition, a tabs or protrusions 2421A, 2421B that extend radially outward from wings 2419A, 2419B of first coupler 2451 are housed within opposing notches or recesses (not shown) formed on the inside of handle 2450 in order to lock or secure first coupler 2451 and push rod 2482 coupled thereto in an extended configuration and prevent proximal retraction of these components during the continued operation of suture connector placement device 2402.

Once plug 2408 has been extended or relocated into sleeve 2406, intermediate shaft 2474 is proximally retracted in order to release sleeve 2406 onto plug 2408. More particularly, when it is desired to complete deployment of suture connector 2404, slider 2454 is proximally retracted in order to proximally retract intermediate shaft 2474 away from sleeve 2406 as shown in FIGS. 37-39. FIG. 37 is a side sectional view of suture connector placement device 2402, and FIGS. 38 and 39 are enlarged side views of only the distal end of the suture connector placement device.

More particularly, when slider 2454 is proximally retracted or pulled backwards, second coupler 2457 disengages or decouples from first coupler 2451 when knob or boss 2423 of second coupler 2457 exits or is pulled out of notch or recess 2427 of first coupler 2451. As such, at this stage of deployment, second coupler 2457 and first coupler 2451 are no longer coupled together and first coupler 2451 and push rod 2482 attached thereto remain stationary in the extended position during retraction of second coupler 2457. However, second coupler 2457 is coupled to lead 2430 via tabs or protrusions 2465A, 2465B at the distal ends of rails 2461A, 2461B of second coupler 2457 being engaged or extending into notches 2440A, 2440B of lead 2430 as described above and thus lead 2430 moves with second coupler 2457 when the second coupler is retracted. Stated another way, when slider 2454 and second coupler 2457 attached thereto are proximally retracted or pulled backward, lead 2430 and intermediate shaft 2474 attached thereto are also proximally retracted or pulled backward. Lead 2430 is attached to intermediate shaft 2474 via pegs 2446A, 2446B of tubular overmold portion 2442, which extend into and are housed within lead 2430 to thereby couple lead 2430 to overmold portion 2442 and transmit force between the two components when lead 2430 is proximally retracted or pulled backward. During retraction of intermediate shaft 2474, sleeve 2406 engages or abuts against distal end 2468 of outer shaft 2464 to ensure that sleeve 2406 is not inadvertently retracted with intermediate shaft 2474.

When intermediate shaft 2474 is retracted, flange 2424 and distally-extending crosshair extension 2445 coupled thereto are also retracted until distally-extending crosshair extension 2445 retract out of or are pulled away from crosshair grooves 2415 of handle 2450 and flange 2424 abuts against stopper 2441 formed within a proximal portion of handle 2450. When distally-extending crosshair extension 2445 are housed within crosshair grooves 2415 of handle 2450 during retraction of intermediate shaft 2474, intermediate shaft 2474 is prevented from rotational movement that would otherwise occur due to spiral pathway or threads 2435 of lead 2430. Thus, distally-extending crosshair extension 2445 and crosshair grooves 2415 of handle 2450 prevent rotation of intermediate shaft 2474 during the second stage of deployment. Proximally-extending fingers 2428 are radially spread apart or outward during retraction of intermediate shaft 2474 to allow flange 2424 to pass by directional stopper 2426. Once flange 2424 is positioned proximal to proximal tips 2428A of proximally-extending fingers 2428 as shown in FIG. 37, proximally-extending fingers 2428 spring radially inward to resume their original or pre-formed shape. Flange 2424 is now positioned or sandwiched between stopper 2441 formed within a proximal portion of handle 2450 and proximal tips 2428A of proximally-extending fingers 2428.

Slider 2454 is proximally retracted to the position shown in FIG. 37 such that distal end 2478 of intermediate shaft 2474 is positioned within outer shaft 2464, proximal to proximal ends of plug 2408 and sleeve 2406 as best shown in FIGS. 38-39. With intermediate shaft 2474 removed from between plug 2408 and sleeve 2406, sleeve 2406 is released to contact or clamp onto plug 2408 thereby securing the suture portions (not shown) between the sleeve and the plug. Stated another way, when intermediate shaft 2474 is retracted, sleeve 2406 is no longer in contact with the outer surface of intermediate sleeve 2474 and sleeve 2406 thereby releases onto plug 2408, thereby enveloping, covering, wrapping around or otherwise surrounding plug 2408. When sleeve 2406 is released onto plug 2408, radial protrusions 2409 of plug 2408 may compress or flatten due to the contact between the sleeve and the plug, thereby ensuring an interference or press fit there-between. Radial protrusions 2409 of plug 2408 also act as force concentrators and/or may cause the suture portions to take a slightly tortuous path. In an embodiment hereof, sleeve 2406 is formed from a resilient or elastic material such as but not limited to an elastomer or Elasthane 80A Thermoplastic Polyether Urethane (TPU) as described above. In the loaded configuration of suture connector 2404 discussed above, sleeve 2406 is stretched or expanded over intermediate shaft 2474 and when intermediate shaft 2474 is retracted, sleeve 2406 resiliently contracts or compresses onto plug 2408. At this point in the method of use, slider 2454 is in a partially retracted position, intermediate shaft 2474 is in a retracted position and suture connector 2404 is in a fully deployed configuration since plug 2408 is in contact with sleeve 2406 with the suture portions sandwiched there-between. Stated another way, when sleeve 2406 is released onto plug 2408, the suture portions extending between the plug and the sleeve are thereby secured or fixed relative to each other within the formed suture connector 2404.

Upon retraction of intermediate shaft 2474, suture connector 2404 extends from distal end 2468 of outer shaft 2464 of suture connector placement device 2402 and has been decoupled therefrom. The sutures, however, are still positioned through the distal end of suture connector placement device 2402. Since the sutures are still positioned through aligned side ports 2470, 2479 of outer shaft 2464, intermediate shaft 2474, respectively, the sutures may function as a suture rail to guide suture connector placement device 2402 down to the formed suture connector 2404 to further cinch suture connector 2404 in a downward direction, against the vessel. For example, a guidewire may be previously positioned through the arteriotomy. A physician may not want to remove the guidewire until after suture connector 2404 is formed. Once suture connector 2404 is formed, the guidewire may be removed and, as described above, the sutures extending through side window 2479 of intermediate shaft 2474 may function as a suture rail to guide suture connector placement device 2402 down to the formed suture connector 2404 to further cinch suture connector 2404 in a downward direction, against the vessel, to ensure full or complete hemostasis of the arteriotomy. Notably, upon retraction of intermediate shaft 2474, the distal ends of pushrod 2482 and intermediate shaft 2474 are both flush with distal end 2468 of outer shaft 2464, thereby creating a blunt pushing feature when the sutures are functioning as a suture rail to guide suture connector placement device 2402 down to the formed suture connector 2404. Thus, advantageously, suture portions that are still disposed within the distal end of suture connector placement device 2402 may still be adjusted or tightened at this stage of operation. Stated another way, due to suture portions forming a suture rail via side window 2479 of intermediate shaft 2474 and the distal end of the device forming blunt pushing feature, the sutures may be tightened post-deployment of the formed suture connector 2404. The sutures may essentially be tightened at any point prior to trimming of the suture portions.

Further, since it is not required to push or eject suture connector 2404 from suture connector placement device 2402, suture connector 2404 may be formed from less rigid or less stiff materials than would otherwise be required if suture connector 2404 had to be pushed or ejected from suture connector placement device 2402. In addition to the material of suture connector 2404, other advantages flow or result from the fact sleeve 2406 is resiliently released onto plug 2408 via retraction of the intermediate shaft and there is no requirement to push or eject the formed connector out of the device. More particularly, pushing or ejecting the formed connector out of the suture connector placement device may result in pushing the suture connector through arteriotomy $V_A$ in the vessel wall $V_W$ of a vessel. If inadvertently pushed through the arteriotomy, suture connector 2404 may contact and damage the inner vessel wall opposite the incision/arteriotomy. Further, if inadvertently pushed through the arteriotomy, suture connector 2404 may not result in full closure and hemostasis at the treatment site.

Once suture connector 2404 is formed in situ, i.e., after a plug is in contact with a sleeve with suture portions sandwiched there-between, slider 2454 is continued to be retracted or further retracted in order to rotate intermediate shaft 2474 and thereby trim the suture portions (not shown) which are still positioned through aligned side ports 2470, 2479 of outer shaft 2464, intermediate shaft 2474, respectively. Stated another way, once final positioning of formed suture connector 2404 is confirmed, the physician can perform the final step of trimming the sutures by rotating intermediate shaft 2474 while applying tension on the sutures via pulling the sutures. More particularly, at this stage of operation, lead 2430 is coupled to the proximal end of intermediate shaft 2474 to permit rotation thereof. Perspective and side views, respectively, of lead 2430 are shown in FIGS. 44 and 45, respectively. Lead 2430 is a tubular component which defines lumen 2432 there-through. An outer surface 2438 of lead 2430 includes opposing flattened surfaces 2436A, 2436B on a proximal end thereof for guiding rails 2461A, 2461B of second coupler 2457 distally over lead 2430 during the first stage of operation as described above. Outer surface 2438 also includes opposing notches or recesses 2440A, 2440B at a distal end of each flattened surface 2436A, 2436B, and notches or recesses 2440A, 2440B are configured to receive or house tabs or protrusions 2465A, 2465B positioned on the distal ends of rails 2461A, 2461B in order to couple second coupler 2457 to lead 2430 as described above.

An inner surface 2434 of lead 2430 includes two opposing spiral pathways or threads 2435 formed thereon as shown on FIG. 45. In another embodiment (not shown), inner surface 2434 of lead 2430 may include a single spiral pathway or thread or more than two spiral pathways or threads 2435 formed thereon. As described above, intermediate shaft 2474 includes tubular overmold portion 2442 formed over the proximal end thereof that includes opposing pegs or bosses 2446A, 2446B which radially extends from an outer surface 2444 thereof. Opposing pegs or bosses 2446A, 2446B are sized or configured to be received or housed within opposing spiral pathways or threads 2435. Stated another way, opposing pegs or bosses 2446A, 2446B has a width approximately equal to the width of spiral pathways or threads 2435. As shown in FIG. 40, flange 2424 of overmold portion 2442 coupled to the outer surface of intermediate shaft 2474 is positioned or sandwiched between stopper 2441 formed within a proximal portion of handle 2450 and proximal tips 2428A of proximally-extending fingers 2428. Further, after the second stage of operation in which intermediate shaft 2474 is retracted, distally-extending crosshair extension 2445 is no longer housed within or constrained by crosshair grooves 2415 of handle 2450. With distally-extending crosshair extension 2445 no longer being housed within crosshair grooves 2415 of handle 2450, intermediate shaft 2474 is now permitted to rotate due to spiral pathways or threads 2435 of lead 2430.

When slider 2454 and second coupler 2457 attached thereto are continued to be proximally retracted or further retracted, lead 2430 (which is coupled to second coupler 2457 via tabs or protrusions 2465A, 2465B at the distal ends of rails 2461A, 2461B of second coupler 2457 being engaged or extending into notches 2440A, 2440B of lead 2430) is also proximally retracted. However, since intermediate shaft 2474 is no longer prevented from rotation due to distally-extending crosshair extension 2445 no longer being housed within or constrained by crosshair grooves 2415 of handle 2450, the interaction between opposing pegs or bosses 2446A, 2446B of overmold portion 2442 and spiral pathways or threads 2435 of lead 2430 causes intermediate shaft 2474 to rotate about or relative to outer shaft 2464 and push rod 2482. More particularly, as lead 2430 is proximally retracted over overmold portion 2442, opposing pegs or bosses 2446A, 2446B of overmold portion 2442 follow spiral pathways or threads 2435 of lead 2430 similar to a cam follower mechanism. Intermediate shaft 2474 is twisted or rotated about its own longitudinal axis and axial movement is not permitted with flange 2424 of overmold portion 2442 coupled to the outer surface of intermediate shaft 2474 abutting against stopper 2441 formed within a proximal portion of handle 2450. By not permitting intermediate shaft 2474 to slide or move axially during rotation thereof, the user has control over the length of suture that is left after trimming and thus there is a tight tolerance on the amount of suture left behind.

When intermediate shaft 2474 is rotated relative to outer shaft 2464, side ports 2470, 2479 of outer shaft 2464, intermediate shaft 2474, respectively are no longer circumferentially aligned. More particularly, as shown in FIG. 41 and FIG. 43, side window 2479 of intermediate shaft 2474 rotates relative to side port 2470 of outer shaft 2464 and the suture portions become trapped within a relatively small gap or port 2499 formed by overlapping side ports 2470, 2479 of outer shaft 2464, intermediate shaft 2474, respectively. With tension applied to the sutures, the sutures run or extend through the relatively small gap or port 2499 against one of cutting surfaces 2496A, 2496B formed on side port or window 2479 of intermediate shaft 2474 and the cutting surface thereby trims or severs the suture portions adjacent to where they extend out of side port 2470 of outer shaft 2464. If any of the suture portions are not cut during a first attempt, the physician can distally advance slider 2454 and attempt the trimming step over and over again until the suture portions are trimmed by the cutting surface. If multiple trimming attempts are made and slider 2454 is distally advanced, intermediate shaft 2474 is prevented from longitudinal movement due to proximal tips 2428A of proximally-extending fingers 2428 of directional stopper 2426 so that distally-extending crosshair extension 2445 of overmold portion 2442 does not re-engage into crosshair grooves 2415 of handle 2450 (which would thereby prevent rotational movement of intermediate shaft 2474 during the subsequent trimming attempt).

Figure 46:
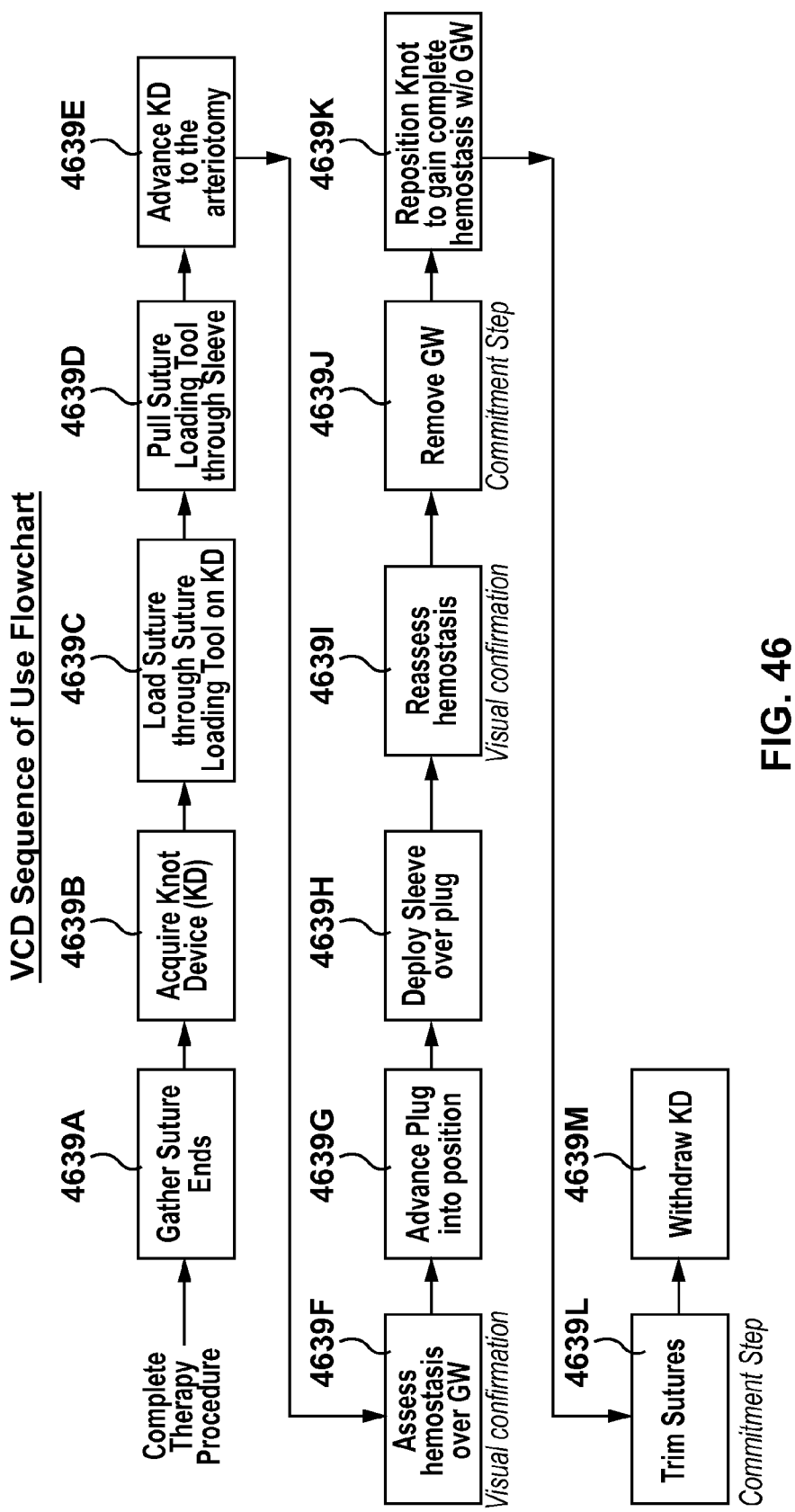
FIG. 46 is a flow chart of a method of use for the suture connector placement device of FIG. 24.

FIG. 46 is a flow chart of a method of use for the suture connector placement device of FIG. 24. Prior to performing a therapy procedure or after a therapy procedure is completed, a suture is introduced into the patient for the purpose of drawing together tissue portions, which may, for example, be the result if an internal wound or an arteriotomy in a blood vessel or an organ. More particularly, in some cases, medical suturing systems are utilized to "pre-close" the arteriotomy $V_A$ by positioning one or more stitches adjacent to an interventional device (such as a catheter) that result in hemostasis of the arteriotomy $V_A$ around the interventional device during the procedure. After the procedure is completed and the interventional device(s) are removed, the stitches positioned by the medical suturing system are utilized to fully close the arteriotomy $V_A$. In other cases, i.e., when the size of the arteriotomy is relatively small, such pre-closure is not required and a medical suturing system or other technique is utilized to close the arteriotomy after the interventional device(s) are removed. After the interventional device is removed, a guidewire from the therapy procedure and/or a guidewire utilized in positioning of the suture may still extend through the arteriotomy. The suture ends are gathered at step 4639A, suture connector placement device 2402 is acquired at step 4639B, and the suture ends are loaded through a suture loading tool or threader which may be included on suture connector placement device 2402 at step 4639C. The suture loading tool is pulled through sleeve 2406 and the suture ends are thereby loaded into suture connector placement device 2402 at step 4639D. Suture connector placement device 2402 is advanced to the arteriotomy at step 4639E, and hemostasis over the guidewire (if present) is accessed at step 4639F. Plug 2408 is then deployed via distal advancement of push rod 2482 at step 4639G as described with respect to FIGS. 34-36 above, and then sleeve 2406 is deployed over plug 2408 via retraction of intermediate shaft 2474 at step 4639H as described with respect to FIGS. 37-39. Hemostasis is reassessed at step 4639I, and the guidewire (if present) is then removed at step 4639J. As described above, after the guidewire is removed, the sutures may function as a suture rail to guide suture connector placement device 2402 down to the formed suture connector 2404 to further cinch suture connector 2404 in a downward direction, against the vessel, to ensure full or complete hemostasis of the arteriotomy at step 4639K. Stated another way, the formed suture connector 2404 is repositioned to gain complete hemostasis without the guidewire extending through the arteriotomy. The sutures are then trimmed via rotation of intermediate shaft 2474 at step 4639L as described above with respect to FIGS. 40-45, and then suture connector placement device 2402 is withdrawn or removed from the patient at step 4639M, leaving the formed suture connector 2404 in situ.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for forming a suture connector in situ comprising:
    a suture connector placement device including,
        a handle having an actuating mechanism,
        an outer shaft defining a lumen from a proximal end to a distal end thereof, wherein the proximal end of the outer shaft is coupled to the handle and wherein the outer shaft includes a side opening;
        an intermediate shaft defining a lumen from a proximal end to a distal end thereof, wherein the intermediate shaft is slidingly disposed within the lumen of the outer shaft with the proximal end of the intermediate shaft being coupled to the actuating mechanism of the handle,
        a push rod slidingly disposed within the lumen of the intermediate shaft, wherein the proximal end of the push rod is coupled to the actuating mechanism of the handle; and
    a suture connector including a sleeve and a plug,
        wherein when the suture connector is in a loaded configuration, the sleeve of the suture connector is disposed on an outer surface of the intermediate shaft via an interference fit there-between and extends from the distal end of the outer shaft and the plug of the suture connector is slidably disposed within the lumen of the intermediate shaft proximal of the sleeve.

2. The system of claim 1, wherein the intermediate shaft includes a window adjacent to the distal end thereof that includes a cutting surface operable to sever at least one suture portion.

3. The system of claim 2, wherein the cutting surface gradually sharpens from an inner surface of the intermediate shaft to an outer surface of the intermediate shaft.

4. The system of claim 2, wherein the intermediate shaft is rotatable relative to the outer shaft and rotation of the intermediate shaft trims the at least one suture portion between the cutting surface of the window of the intermediate shaft and the side opening of the outer shaft.

5. The system of claim 4, wherein the actuating mechanism permits distal advancement of the push rod relative to the intermediate shaft to slide the plug within the lumen of the intermediate shaft until the plug is longitudinally positioned within the sleeve, permits proximal retraction of the intermediate shaft relative to the push rod to free the sleeve from contact with the intermediate shaft such that the sleeve releases onto the plug, and also permits rotation of the intermediate shaft relative to the outer shaft.

6. The system of claim 1, wherein the intermediate shaft includes a plurality of side openings that extend in a proximal direction from the distal end thereof that are configured to increase the flexibility of the distal end of the intermediate shaft and wherein when the suture connector is in a loaded configuration, the sleeve of the suture connector is disposed on the outer surface of the intermediate shaft over the plurality of side openings thereof, thereby compressing the plurality of side openings of the intermediate shaft.

7. The system of claim 1, wherein the sleeve is formed from Elasthane 80A Thermoplastic Polyether Urethane (TPU).

8. The system of claim 7, wherein the plug is formed from a material that is harder than the sleeve.

9. The system of claim 1, wherein the intermediate shaft is formed from a stainless steel hypotube.

10. A system for forming a suture connector in situ comprising:
    a suture connector placement device including,
        a handle having an actuating mechanism,
        an outer shaft defining a lumen from a proximal end to a distal end thereof, wherein the proximal end of the outer shaft is coupled to the handle and wherein the outer shaft includes a side opening,
        an intermediate shaft defining a lumen from a proximal end to a distal end thereof, wherein the intermediate shaft is slidingly disposed within the lumen of the outer shaft with the proximal end of the intermediate shaft being coupled to the actuating mechanism of the handle, the actuating mechanism being configured to proximally retract the intermediate shaft, and wherein the intermediate shaft includes a plurality of side openings, each side opening being of a preformed width and extending in a proximal direction from the distal end of the intermediate shaft,
        a push rod slidingly disposed within the lumen of the intermediate shaft, wherein the proximal end of the push rod is coupled to the actuating mechanism of the handle, the actuating mechanism being configured to distally advance the push rod; and
    a suture connector including a sleeve formed of a resilient material and a plug,
        wherein when the suture connector is in a loaded configuration, the sleeve of the suture connector is disposed on an outer surface of the intermediate shaft over the plurality of side openings thereof, thereby compressing the plurality of side openings of the intermediate shaft and reducing their pre-formed widths, and the plug of the suture connector is slidably disposed within the lumen of the intermediate shaft proximal of the sleeve, and
        wherein distal advancement of the push rod moves the plug to longitudinally position the plug within the sleeve, thereby expanding the plurality of side openings of the intermediate shaft to return to their pre-formed widths, and proximal retraction of the intermediate shaft releases the sleeve onto the plug.

11. The system of claim 10, wherein the intermediate shaft is rotatable relative to the outer shaft and includes a window adjacent to the distal end thereof, the window of the intermediate shaft including a cutting surface operable to sever at least one suture portion such that rotation of the intermediate shaft trims the at least one suture portion between the cutting surface of the window of the intermediate shaft and the side opening of the outer shaft.

12. The system of claim 11, wherein the cutting surface gradually sharpens from an inner surface of the intermediate shaft to an outer surface of the intermediate shaft.

13. The system of claim 11, wherein the actuating mechanism permits distal advancement of the push rod relative to the intermediate shaft to slide the plug within the lumen of the intermediate shaft until the plug is longitudinally positioned within the sleeve, permits proximal retraction of the intermediate shaft relative to the push rod to free the sleeve from contact with the intermediate shaft such that the sleeve releases onto the plug, and also permits rotation of the intermediate shaft relative to the outer shaft.

14. The system of claim 10, wherein the intermediate shaft is formed from a stainless steel hypotube.

15. A system for forming a suture connector in situ comprising:
   a suture connector placement device including,
      a handle having an actuating mechanism,
      an outer shaft defining a lumen from a proximal end to a distal end thereof, wherein the proximal end of the outer shaft is coupled to the handle and wherein the outer shaft includes a side opening,
      an intermediate shaft defining a lumen from a proximal end to a distal end thereof, wherein the intermediate shaft is slidingly and rotatably disposed within the lumen of the outer shaft with the proximal end of the intermediate shaft being coupled to the actuating mechanism of the handle, the intermediate shaft including a window adjacent to the distal end thereof, the window of the intermediate shaft including a cutting surface operable to sever at least one suture portion,
      a push rod slidingly disposed within the lumen of the intermediate shaft, wherein the proximal end of the push rod is coupled to the actuating mechanism of the handle; and
   a suture connector including a sleeve and a plug,
      wherein when the suture connector is in a loaded configuration, the sleeve of the suture connector is concentrically disposed over an outer surface of the intermediate shaft and the plug of the suture connector is slidably disposed within the lumen of the intermediate shaft proximal of the sleeve.

16. The system of claim 15, wherein rotation of the intermediate shaft trims the at least one suture portion between the cutting surface of the window of the intermediate shaft and the side opening of the outer shaft.

17. The system of claim 16, wherein the cutting surface gradually sharpens from an inner surface of the intermediate shaft to an outer surface of the intermediate shaft.

18. The system of claim 15, wherein the intermediate shaft includes a plurality of side openings that extend in a proximal direction from the distal end thereof that are configured to increase the flexibility of the distal end of the intermediate shaft.

19. The system of claim 18, wherein when the suture connector is in a loaded configuration, the sleeve of the suture connector is disposed on the outer surface of the intermediate shaft over the plurality of side openings thereof, thereby compressing the plurality of side openings of the intermediate shaft.

20. The system of claim 15, wherein the actuating mechanism permits distal advancement of the push rod relative to the intermediate shaft to slide the plug within the lumen of the intermediate shaft until the plug is longitudinally positioned within the sleeve, permits proximal retraction of the intermediate shaft relative to the push rod to free the sleeve from contact with the intermediate shaft such that the sleeve releases onto the plug, and also permits rotation of the intermediate shaft relative to the outer shaft.

* * * * *